US009068182B2

(12) United States Patent
Deshayes et al.

(10) Patent No.: US 9,068,182 B2
(45) **Date of Patent: *Jun. 30, 2015**

(54) SYNTHETIC POLYSACCHARIDE MICROCARRIERS FOR CULTURING CELLS

(75) Inventors: Sophie Deshayes, Rampillon (FR); David Henry, Morigny-Champigny (FR); Martial Hervy, Thomery (FR)

(73) Assignee: Corning Incorporated, Corning, NY (US)

( * ) Notice: Subject to any disclaimer, the term of this patent is extended or adjusted under 35 U.S.C. 154(b) by 96 days.

This patent is subject to a terminal disclaimer.

(21) Appl. No.: 12/845,550

(22) Filed: Jul. 28, 2010

(65) Prior Publication Data

US 2012/0058554 A1 Mar. 8, 2012

Related U.S. Application Data

(60) Provisional application No. 61/229,114, filed on Jul. 28, 2009.

(30) Foreign Application Priority Data

Feb. 26, 2010 (EP) .................................... 10305203

(51) Int. Cl.

| | |
|---|---|
| ***G01N 33/53*** | (2006.01) |
| ***G01N 21/64*** | (2006.01) |
| ***G01N 21/75*** | (2006.01) |
| ***G01N 21/76*** | (2006.01) |
| ***G01N 21/78*** | (2006.01) |
| ***C12N 11/06*** | (2006.01) |
| ***C12N 5/00*** | (2006.01) |
| ***C12N 5/0735*** | (2010.01) |
| ***C12N 11/10*** | (2006.01) |
| *G01N 31/00* | (2006.01) |
| *G01N 33/573* | (2006.01) |

(52) U.S. Cl.

CPC .............. *C12N 11/06* (2013.01); *C12N 5/0075* (2013.01); *C12N 5/0606* (2013.01); *C12N 11/10* (2013.01); *C12N 2531/00* (2013.01); *C12N 2533/70* (2013.01)

(58) Field of Classification Search

None

See application file for complete search history.

(56) References Cited

U.S. PATENT DOCUMENTS

| | | | | |
|---|---|---|---|---|
| 5,294,551 A * | 3/1994 | Furcht et al. | .................. | 435/402 |
| 5,607,475 A * | 3/1997 | Cahalan et al. | ............... | 424/423 |
| 5,998,184 A * | 12/1999 | Shi | ............................... | 435/176 |
| 6,378,527 B1 * | 4/2002 | Hungerford et al. | .......... | 128/898 |
| 7,022,818 B1 * | 4/2006 | Masure et al. | ................ | 530/350 |
| 7,544,656 B2 * | 6/2009 | Sabetsky | ........................ | 514/1.1 |
| 7,670,839 B2 | 3/2010 | Bouwstra et al. | | |
| 7,951,423 B2 * | 5/2011 | Grater | .......................... | 427/256 |
| 8,637,309 B2 | 1/2014 | Oh et al. | | |
| 8,691,569 B2 | 4/2014 | Oh et al. | | |
| 8,716,018 B2 | 5/2014 | Oh et al. | | |
| 8,828,720 B2 | 9/2014 | Oh et al. | | |
| 2011/0053783 A1 | 3/2011 | Du et al. | | |

FOREIGN PATENT DOCUMENTS

| | | |
|---|---|---|
| JP | 4-278081 | 10/1992 |
| JP | 4-360677 | 12/1992 |
| JP | 5-207873 | 8/1993 |

OTHER PUBLICATIONS

Gebb C et al: "Alternative surfaces for Microcarrier culture of animal cells." Advances in experimental Medicine and Biology, vol. 172, 1984, pp. 151-167.

Varani J et al: "Use of recombinant and synthetic peptides as attachment factors for cells on Microcarriers." Cytotechnology, vol. 13, No. 2, 1993, pp. 89-98.

Kong D et al: "Cell growth and protein formation on various Microcarriers" Cytotechnology, vol. 29, No. 2, Feb. 1, 1999, pp. 149-156.

Aug. 17, 2010 European extended search report issued in counterpart application No. 10305203.1.

Nov. 18, 2010 International search report issued in counterpart application No. PCT/US2010/046145.

Sep. 20, 2012 European Office Action issued in counterpart application No. 10305203.1.

Sep. 18, 2014 English translation of Japanese Office Action in counterpart application No. 2012-554982.

Chung, Y. et al, "Human Embryonic Stem Cell Lines Generated without Embryo Destruction", Cell Stem Cell, vol. 2, No. 2, Feb. 2008, pp. 113-117.

Dame, M.K. et al, "Recombinant collagen for animal product-free dextran microcarriers", *In Vitro Cell Dev Biol Anim*, 2008, 44(10), pp. 407-414.

Hersel, U. et al, "RGD modified polymers: biomaterials for stimulated cell adhesion and beyond", Biomaterials 24 (2003), pp. 4385-4415.

Lee, M.H. et al, "Biomimetic Carbohydrate Substrates of Tunable Properties Using Immobilized Dextran Hydrogels", *Biomacromolecules* (2008), 9, pp. 2315-2321.

Levesque, S.G. et al, "Synthesis of cell-adhesive dextran hydrogels and macroporous scaffolds", Biomaterials 27 (2006), pp. 5277-5285.

* cited by examiner

*Primary Examiner* — Jon P Weber
*Assistant Examiner* — Kailash C Srivastava
(74) *Attorney, Agent, or Firm* — Susan S. Wilks; Hallie W. Wherley

(57) ABSTRACT

A cell culture polysaccharide microcarrier includes (1) a cross-linked polysaccharide microcarrier base having a neutral or negative charge at pH 7, and (ii) a polypeptide conjugated to the base. The polypeptide may contain a cell adhesive sequence, such as RGD. Cells cultured with such microcarriers exhibit peptide-specific binding to the microcarriers.

20 Claims, 14 Drawing Sheets

E

| Alkaline Phosphatase Activity | |
|---|---|
| +<br>+ | ES-D3 on CMD-VN |
| +<br>+ | ES-D3 on Cytodex3 |
| - | STO on TCT |

SEQUENCE LISTING

```
<160> NUMBER OF SEQ ID NOS: 4

<210> SEQ ID NO 1
<211> LENGTH: 14
<212> TYPE: PRT
<213> ORGANISM: Artificial sequence
<220> FEATURE:
<223> OTHER INFORMATION: Synthetic Peptide

<400> SEQUENCE: 1

Lys Gly Pro Asn Val Thr Arg Gly Asp Val Phe Thr Met Pro
1               5                   10


<210> SEQ ID NO 2
<211> LENGTH: 15
<212> TYPE: PRT
<213> ORGANISM: Artificial sequence
<220> FEATURE:
<223> OTHER INFORMATION: Synthetic Peptide

<400> SEQUENCE: 2

Lys Gly Gly Asn Gly Glu Pro Arg Gly Asp Thr Tyr Arg Ala Tyr
1               5                   10                  15


<210> SEQ ID NO 3
<211> LENGTH: 9
<212> TYPE: PRT
<213> ORGANISM: Artificial sequence
<220> FEATURE:
<223> OTHER INFORMATION: Synthetic Peptide

<400> SEQUENCE: 3

Gly Arg Gly Asp Ser Pro Ile Ile Lys
1               5


<210> SEQ ID NO 4
```

-continued

```
<211> LENGTH: 9
<212> TYPE: PRT
<213> ORGANISM: Artificial sequence
<220> FEATURE:
<223> OTHER INFORMATION: Synthetic Peptide

<400> SEQUENCE: 4

Gly Arg Gly Glu Ser Pro Ile Ile Lys
1               5
```

SYNTHETIC POLYSACCHARIDE MICROCARRIERS FOR CULTURING CELLS

CROSS-REFERENCE TO RELATED APPLICATIONS

This application claims the benefit of priority under 35 U.S.C. §119 of European Patent Application Serial No. 10305203.1 filed on Feb. 26, 2010, and also claims the benefit of priority under 35 U.S.C. §119(e) of U.S. Provisional Application Ser. No. 61/229,114 filed on Jul. 28, 2009.

FIELD

The present disclosure relates to cell culture microcarriers, and more particularly to synthetic, chemically-defined microcarriers.

SEQUENCE LISTING

This application contains a Sequence Listing electronically submitted via EFS-Web to the United States Patent and Trademark Office as text filed named "SP10-045_SEQ_LIST_ST25.txt" having a size of 4-2 kb and created on Nov. 17, 2011. Due to the electronic filing of the Sequence Listing, the electronically submitted Sequence Listing serves as both the paper copy required by 37 CFR §1.821(c) and the CRF required by §1.821(e). The information contained in the Sequence Listing is hereby incorporated herein by reference.

BACKGROUND

Microcarriers provide an alternative for large-scale cell culture. Microcarriers are typically stirred in cell culture media and provide a very large surface to area ratio for cell growth. Microcarriers can provide substantially higher cell yields per culture volume relative to conventional equipment.

For anchorage-dependent cells, microcarriers having positively charged surfaces have been shown to provide excellent adhesion and growth. However, cell harvesting may be difficult in proportion to the robustness of the adhesion and generally requires harsh protease treatment that may have deleterious effects on cells. In addition, such microcarriers can suffer from loss of cells and lack of reproducibility in stirred culture. Microcarrier toxicity and nutrient absorption have been identified as causes of these difficulties. Moreover, to achieve good cell attachment and proliferation charge density should be optimized. These problems have been partially overcome by coating the microcarriers, treating with a sequence of chemical or physical steps to reduce the charge, adding carboxymethyl cellulose, or soaking the beads in serum. While successful, such pretreatment of the carrier is time consuming introduces variability.

Some microcarriers have been designed to enable appropriate adhesion without extensive tuning of surface charges density. For example, microcarriers have been prepared to present specific polypeptide sequences at the surface, which polypeptides are configured to provide specific interaction with adhesion receptor of the cells. Examples of such microcarriers include gelatin or collagen linked to dextran beads or to polystyrene beads. While having various advantages, such microcarriers are made of animal derived materials and are not suitable for culturing cells dedicated to cell therapies due to the risk of xenogenic contamination through, for example, pathogen proteins or viruses.

To solve this issue, recombinant proteins or polypeptides have been synthesized and coated onto microcarriers. While such microcarries have the advantage of being free of animal derived components, they may have several drawbacks. For example, some microcarriers have been shown not only to bind cells, but also to activate cells, which means that the cell surface and cytoskeletal proteins have rearranged and specific genes have been induced to result in spreading and proliferation. Such activation may not be desirable when culturing cells, such as pluripotent stem cells. In addition, the level of cell adhesion with some of these beads may not be sufficiently high for robust culture of some anchorage-dependent cells, particularly when serum-free, chemically-defined media are used. When serum-free media are used, the media do not provide adhesion proteins, which can bind to the microcarrier surface and thus facilitate binding of cells. The absence of serum especially presents problems when using cells that produce little extracellular matrix, such as certain stem cells, including embryonic stem cells.

A good number of positively charged microcarriers, some of which contain associated protein or recombinant polypeptide, are available for use in culturing anchorage-dependent cells. These microcarriers have proven effective for culturing many cells under many conditions. However, they do suffer from the drawbacks described above.

BRIEF SUMMARY

Among other things, the present disclosure describes synthetic, chemically-defined microcarriers that may provide robust and selective binding of anchorage-dependent cells. The microcarriers include a swellable cross-linked polysaccharide microcarrier base having a neutral or negatively charged surface (at pH 6-8). While not intending to be bound by theory, it is believed that the negatively charged surface discourages adhesion of the cells for hydrogel materials, particularly in the absence of serum. The microcarriers described herein also include a polypeptide containing an RGD amino acid sequence conjugated to the surface to mediate cell adhesion. As described herein, such microcarriers allow for selective adhesion of cells via the polypeptide with little or no non-selective binding. Accordingly, the microcarriers described herein may be used to culture anchorage dependent cells in a controlled manner. The microcarriers, despite having neutral or net negative charge, and in some embodiments no positive charge, provide cell attachment of sufficient strength to support culture in a spinner flask. Such microcarriers should be valuable for culture and maintenance of pluripotent stem cells, including human embryonic stem cells, due to the lack of non-selective binding to the carriers.

In various embodiments, the microcarriers are prepared by grafting appropriate polypeptides to carboxylic acid group containing crosslinked polysaccharide microcarriers, such as dextran beads. The remaining non-peptide conjugated carboxylic acid groups, or a portion thereof, may be blocked via derivation with a low molecular weight amine monamine, such as ethanolamine. Such blocking converts highly hydrophilic carboxylic acid groups to less hydrophilic amide group, which decreases the hydrophillicity of the microcarrier and thus alters the equilibrium water content. As a consequence the blocking alters the stiffness of the hydrogel microcarrier material. That is, decreasing the water content increases the stiffness of the microcarrier. Accordingly, the stiffness and swellability of the microcarrier can be readily tuned, as desired, to impact cell behavior, without having to control crosslinking density. Thus, the stiffness may be modified after the microcarrier base has been manufactured (after the cross-linking density has been fixed).

One or more embodiments of the microcarriers or methods described herein provide one or more advantages over prior microcarriers, methods for preparing microcarriers, or methods for culturing cells with microcarriers. For example, the microcarriers described herein are devoid of animal derived materials, which limits the risk of pathogen contamination. This is particularly relevant when the cultured cells are dedicated to cell-therapies. The microcarriers may be monolithic and not coated, and thus are not prone to delamination. Cells can be readily harvested from many of the microcarriers described herein using gentle trypsination or alternative solutions that do not adversely affect the cells. Due to low levels of non-specific binding to the microcarrier base, bioselective cell attachment through receptor binding to polypeptides grafted to the microcarrier can occur. Such highly bioselective attachment may be beneficial for culturing primary cells, hepatocytes, and other cells, such as stem cells including embryonic stem cells. In addition to ready tuning of the stiffness and swellability of the microcarrier, the polypeptide density can be tuned by derivation of the carboxylic acid groups of the microcarrier based. In many embodiments, the microcarriers are highly transparent relative to, for example, polystyrene-based microcarriers and allow easy microscopic examination of attached cells. These and other advantages will be readily understood from the following detailed descriptions when read in conjunction with the accompanying drawings.

Figure 1:
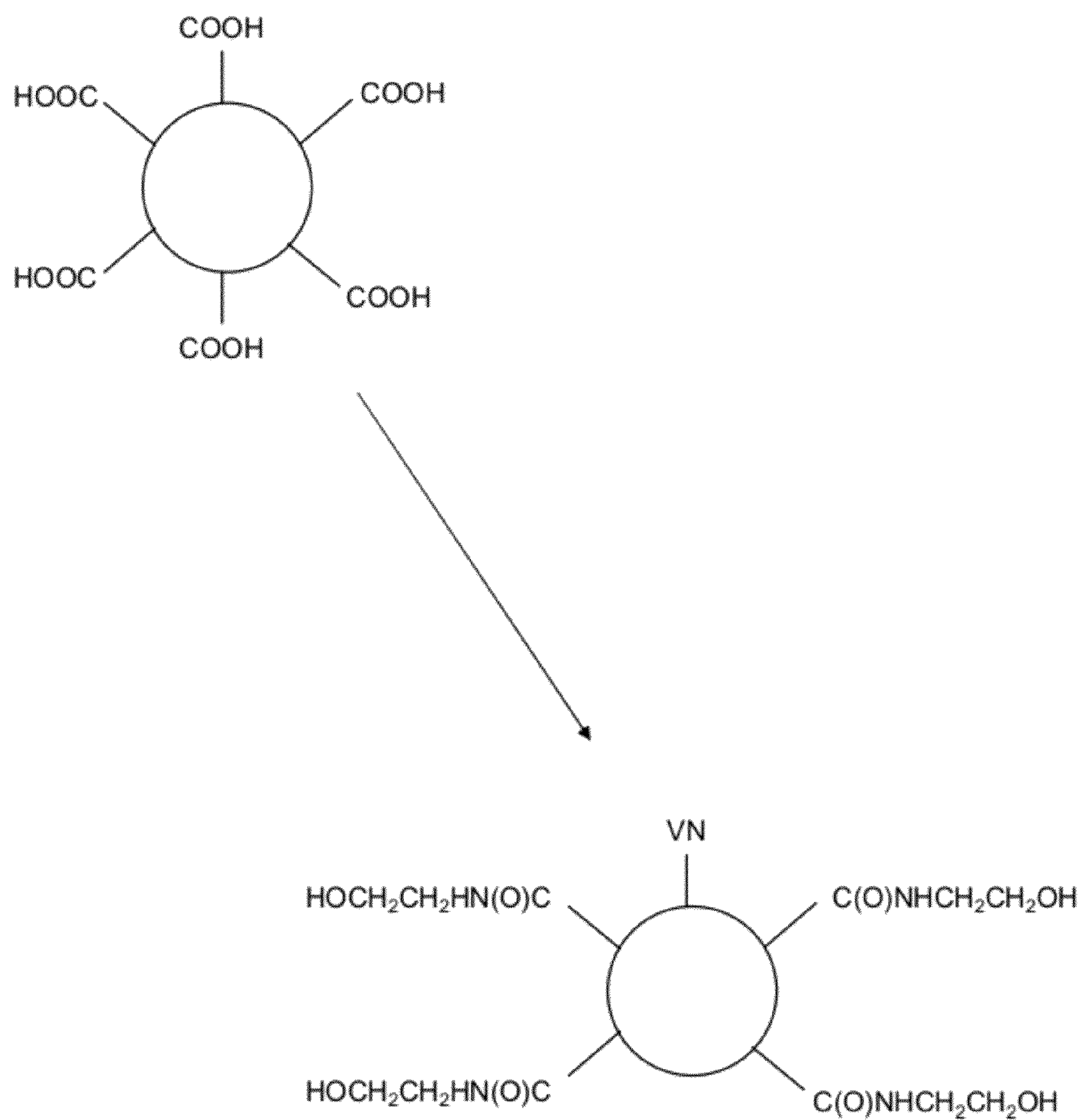
FIG. 1 is a scheme showing the peptide conjugation and blocking reaction performed on chemically crosslinked dextran beads. For the sake of simplicity one grafted peptide only and some amide groups (resulting of the blocking step) have been represented.

The schematic drawings in are not necessarily to scale. Like numbers used in the figures refer to like components, steps and the like. However, it will be understood that the use of a number to refer to a component in a given figure is not intended to limit the component in another figure labeled with the same number. In addition, the use of different numbers to refer to components is not intended to indicate that the different numbered components cannot be the same or similar.

DETAILED DESCRIPTION

In the following detailed description, reference is made to the accompanying drawings that form a part hereof, and in which are shown by way of illustration several specific embodiments of devices, systems and methods. It is to be understood that other embodiments are contemplated and may be made without departing from the scope or spirit of the present disclosure. The following detailed description, therefore, is not to be taken in a limiting sense.

All scientific and technical terms used herein have meanings commonly used in the art unless otherwise specified. The definitions provided herein are to facilitate understanding of certain terms used frequently herein and are not meant to limit the scope of the present disclosure.

As used in this specification and the appended claims, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising" and the like.

As used herein, "providing" an object or compounds means using, making or otherwise obtaining the object or compound.

Polypeptide sequences are referred to herein by their one letter amino acid codes and by their three letter amino acid codes. These codes may be used interchangeably.

As used herein, "peptide" and "polypeptide" mean a sequence of amino acids that may be chemically synthesized or may be recombinantly derived, but that are not isolated as entire proteins from animal sources. For the purposes of this disclosure, peptides and polypeptides are not whole proteins. Peptides and polypeptides may include amino acid sequences that are fragments of proteins. For example peptides and polypeptides may include sequences known as cell adhesion sequences such as RGD. Polypeptides may be of any suitable length, such as between three and 30 amino acids in length. Polypeptides may be acetylated (e.g. Ac-LysGlyGly) or amidated (e.g.SerLysSer-$NH_2$) to protect them from being broken down by, for example, exopeptidases. It will be understood that these modifications are contemplated when a sequence is disclosed.

As used herein, "microcarrier" means a small discrete particle for use in culturing cells and to which cells may attach. Microcarriers may be in any suitable shape, such as rods, spheres, and the like, and may be porous or non-porous.

A "microcarrier base", as used herein, means a polymeric microcarrier on which a polypeptide may be conjugated.

As used herein, a "polysaccharide" means a polymer having a backbone of linked monosaccharide units. It will be understood that pendant moieties of a polysaccharide may be substituted, as desired, relative to the native monosaccharide. A polysaccharide may include components that do not originate from, or that are not derived from, a monosaccharide, such as a cross-linking component originating from a non-monosaccharide cross-linking agent (e.g., a di- or higher functional monomer or oligomer). In some cases, a polysaccharide may be cross-linked via compounds originating from monosaccharides or oligosaccharides.

As used herein, "hydrogel" means a polymer that can absorb water in an amount greater than or equal to 30% of its dry weight. In many embodiments, a hydrogel can absorb water in an amount greater than or equal to 100% of its dry weight. It will be understood that the amount of water that a hydrogel polymer can absorb may vary depending on the degree that the polymer is crosslinked, where greater crosslinking often leading to less water absorption or swelling.

As used herein, "equilibrium water content" refers to water-absorbing characteristic of a polymeric material, such as a polysaccharide, and is defined and measured by equilibrium water content (EWC) as shown by Formula 1:

$$EWC(\%)=[(W\text{gel}-W\text{dry})/(W\text{gel})]*100. \quad \text{Formula 1:}$$

The present disclosure describes, inter alia, synthetic microcarriers for culturing cells. The microcarriers may be formed from conjugating polypeptides to carboxylic acid functional groups of a cross-linked polysaccharide base. At least a portion of the carboxylic acid functional groups may be blocked by derivation with a low molecular weight monoamine. The resulting microcarriers have a neutral or negatively charged surface, and provide polypeptide-selective binding with cells in culture.

1. Microcarrier

A microcarrier, as described herein, includes a microcarrier base and a polypeptide conjugated to the base. The microcarrier base is a cross-linked polysaccharide having a neutral or negatively charged surface at pH levels typically present during cell culture, such as between pH 6 and 8. In many embodiments, the base is free from positively charged moieties under such pH conditions.

In general, it is preferred that microcarriers have a density slightly greater than the cell culture medium in which they are to be suspended to facilitate separation of the microcarriers from the surrounding medium. In various embodiments, the microcarriers have a density of about 1.01 to 1.10 grams per cubic centimeter. Microcarriers having such a density should be readily maintained in suspension in cell culture medium with gentle stirring.

In addition, it is preferred that the size variation of the microcarriers is small to ensure that most, if not all, of the microcarriers can be suspended with gentle stirring. By way of example, the geometric size distribution of the microcarriers may be between about 1 and 1.4. Microcarriers may be of any suitable size. For example, microcarriers may have a diametric dimension of between about 20 microns and 1000 microns. Spherical microcarriers having such diameters can support the attachment of several hundred to thousands of cells per microcarrier.

A. Microcarrier Base

Any suitable cross-linked polysaccharide may be used to form the base. For example, agarose, starch, dextran, cellulose, or polyglucose beads may serve to form the microcarrier base. More generally, almost any hydrogel-forming polysaccharide may be used. Carboxylic acid groups may be introduced by any suitable derivation reaction, e.g. as described below, to provide a surface with negative charge (at cell culture pH) and to provide a moiety for conjugation of a polypeptide, e.g. as described below. In some embodiments, polysaccharides having carboxylic acid pendant moieties may be used without further derivatization. For example, alginic acid (also called alginate) is a gel-forming polysaccharide naturally containing carboxylic acid groups.

Any suitable method may be used to prepare a bead or other particle for forming the microcarrier base. For example, cross-linked polysaccharide beads or particles may be prepared as described in, for example, (i) U.S. Pat. No. 3,002,823 to Flodin et al., Process of separating materials having different molecular weights and dimensions, Oct. 3, 1961, or (ii) U.S. Pat. No. 3,208,994 to Flodin, Process for preparing hydrophilic copolymerization and product obtained thereby, Sep. 28, 1965. The particles may then be derivatized with carboxylic acid groups, e.g. as described below, to form the microcarrier base.

Of course, cross-linking of a polysaccharide may be performed in any suitable manner, such as chemically or physically. Preferably the crosslinking is covalent. Nearly any known or future developed cross-linking agent may be used. Some examples of suitable cross-linking agents include divinyl sulphone and other crosslinking vinyl compounds; epihalohydrins, such as epichlorohydrin and epibromohydrin; epoxides, bisepoxides and trisepoxides. See, for example, U.S. Pat. No. 5,135,650 go Hjerten and Liao, Chromatography stationary phase material for high performance liquid chromatography, Aug. 4, 1992.

Suitable methods for forming cross-linked dextran beads are described in U.S. Pat. No. 4,794,177 to Peska et al., Method for the production of bead dextran materials for gel chromatography, Dec. 27, 1988. Of course, a number of suitable gel-forming cross-linked polysaccharide beads may be purchased from commercial vendors, such as GE Healthcare Bio-Scicences, Sigma-Aldrich, Dow and Aqulon. Sephadex® beads from GE Healthcare Bio-Sciences are an example of suitable dextran beads that may be used.

To the extent that the beads or particles do not contain pendant carboxylic acid functional groups, the beads or particles may be derivatized to include such groups. Any suitable method may be used to derivatize the particles to form a microcarrier base having carboxylic acid functional groups. Some methods for introcuding carboxylate function into a polysaccharide backbone include reaction with chloroacetic acid, chloropropionic acid, bromohexanoic acid, succinic anhydride, glutaric anhydride, maleic anhydride, citraconic anhydride, or the like.

Examples of microcarrier bases that have carboxylic acid functional groups include carboxymethylated dextran beads (e.g., CM Sephadex beads from GE Healthcare Bio-Sciences), succinylated dextran beads, and the like.

In various embodiments, the content of carboxylic acid groups before peptide grafting is between about 1.5 milliequivalents (meq)/g and about 5 meq/g, such as between 4 meq/g and 5 meq/g.

The water regain of the microcarrier material before derivatization with the peptide in water at neutral pH is, in many embodiments, more than 10 ml/g, such as between 30 ml/g and 50 ml/g. The term "water regain" is intended to mean the amount of water in grams that can be absorbed by 1 g of the dry product.

It will be understood that the polysaccharide and cross-linker chosen, as well as the relative amounts, and the density of carboxylic acid functional groups present will affect the desired properties of the resulting microcarrier, such as the water regain or equilibrium water content (EWC). For example, higher degrees of hydrophobicity of the polysaccharide, higher densities of the carboxylic acid derivatization, and lower degrees of crosslinking tend to result in higher water regains and higher EWCs. Thus, the water regain and EWC of a microcarrier base can be tuned by selecting appropriate polysaccharides, cross-linking agents, and controlling COOH derivatization.

While not intending to be bound by theory, it is believed that the EWC of the polymeric microcarrier may be an important variable in determining what types of cells the microcarrier can support in culture. The stiffness and swelling power of the microcarrier may mimic environments in which certain cells grow well. As presented in co-pending patent applications, (i) U.S. Patent Application Publication No. 2009/0191627, Fadeev et al, Synthetic surfaces for culturing cells in chemically defined media, published Jul. 30, 2009 and (ii) U.S. Patent Application Publication No. 2009/0191632, Fadeev et al., Swellable (meth)acrylate surfaces for culturing cells in chemically defined media, published Jul. 30, 2009, swellable surfaces having an EWC of between about 5% and about 70% were suitable for culturing human embryonic stem cells in an undifferentiated state for at least five passages. Accordingly, in various embodiments, a microcarrier as described herein has an EWC of between about 5% and about 70%. In various embodiments, the EWC of a microcarrier in distilled, deionized water is between 5% and 70%, between 5% and 60%, between 5% and 50%, between 5 and 40%, between 5% and 35%, between 10% and 70%, between 10% and 50% between 10 and 40%, between 5% and 35%, between 10% and 35% or between 15% and 35% in water.

As discussed further below, one or more polypeptides may be conjugated to microcarrier, which may affect the EWC of the microcarrier (typically increasing the EWC). The amount of polypeptide conjugated to a microcarrier tends to be variable and can change depending on the size (e.g., diameter) of the microcarrier. Accordingly, the EWC of microcarrier with conjugated poypeptide prepared in accordance with a standard protocol may be variable. For purposes of reproducibility, it may be desirable to measure the EWC of microcarriers prior to conjugation with a polypeptide. With this noted, in some embodiments, after the microcarriers have been conjugated with polypeptides, the EWC of embodiments of microcarrier-polypeptide conjugates may be between about 10% and about 40% in water.

Of course, a microcarrier as described herein may have any suitable EWC. In various embodiments, the EWC of the microcarrier is greater than 100% and may be greater than 400% in some embodiments.

B. Conjugation of Polypeptide to Polymeric Microcarrier Base

Any suitable polypeptide may be conjugated to a microcarrier base. Preferably, the polypeptide includes an amino acid capable of conjugating to microcarrier base; e.g. via a free carboxyl group of the base. By way of example, any native or biomimetic amino acid having functionality that enables nucleophilic addition; e.g. via amide bond formation, may be included in polypeptide for purposes of conjugating to the microcarrier base via a carboxylic acid group. Lysine, homolysine, ornithine, diaminoproprionic acid, and diaminobutanoic acid are examples of amino acids having suitable properties for conjugation to a carboxyl group of the microcarrier. In addition, the N-terminal alpha amine of a polypeptide may be used to conjugate to the carboxyl group, if the N-terminal amine is not capped. In various embodiments, the amino acid of polypeptide that conjugates with the microcarrier is at the carboxy terminal position or the amino terminal position of the polypeptide.

In numerous embodiments, the polypeptide, or a portion thereof, has cell adhesive activity; i.e., when the polypeptide is conjugated to the microcarrier base, the polypeptide allows a cell to adhere to the surface of the peptide-containing microcarrier. By way of example, the polypeptide may include an amino sequence, or a cell adhesive portion thereof, recognized by proteins from the integrin family or leading to an interaction with cellular molecules able to sustain cell adhesion. For example, the polypeptide may include an amino acid sequence derived from collagen, keratin, gelatin, fibronectin, vitronectin, laminin, BSP, or the like, or portions thereof. In various embodiments, polypeptide includes an amino acid sequence of ArgGlyAsp (RGD).

Microcarrier bases as described herein provide a synthetic surface to which any suitable adhesion polypeptide or combinations of polypeptides may be conjugated, providing an alternative to biological substrates or serum that have unknown components. In current cell culture practice, it is known that some cell types require the presence of a biological polypeptide or combination of peptides on the culture surface for the cells to adhere to the surface and be sustainably cultured. For example, HepG2/C3A hepatocyte cells can attach to plastic culture ware in the presence of serum. It is also known that serum can provide polypeptides that can adhere to plastic culture ware to provide a surface to which certain cells can attach. However, biologically-derived substrates and serum contain unknown components. For cells where the particular component or combination of components (peptides) of serum or biologically-derived substrates that cause cell attachment are known, those known polypeptides can be synthesized and applied to a microcarrier as described herein to allow the cells to be cultured on a synthetic surface having no or very few components of unknown origin or composition.

For any of the polypeptides discussed herein, it will be understood that a conservative amino acid may be substituted for a specifically identified or known amino acid. A "conservative amino acid", as used herein, refers to an amino acid that is functionally similar to a second amino acid. Such amino acids may be substituted for each other in a polypeptide with a minimal disturbance to the structure or function of the polypeptide according to well known techniques. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E), Asparagine (N), Glutamine (Q).

A linker or spacer, such as a repeating poly(ethylene glycol) linker or any other suitable linker, may be used to increase distance from polypeptide to surface of microcarrier. The linker may be of any suitable length. For example, if the linker is a repeating poly(ethylene glycol) linker, the linker may contain between 2 and 10 repeating ethylene glycol units. In some embodiments, the linker is a repeating poly (ethylene glycol) linker having about 4 repeating ethylene glycol units. All, some, or none of the polypeptides may be conjugated to a microcarrier base via linkers. Other potential linkers that may be employed include polypeptide linkers such as poly(glycine) or poly(β-alanine).

A polypeptide may be conjugated to the microcarrier at any density, preferably at a density suitable to support culture of undifferentiated stem cells or other cell types. Polypeptides may be conjugated to a microcarrier base at a density of between about 1 pmol per $mm^2$ and about 50 pmol per $mm^2$ of surface of the microcarrier. For example, the polypeptide may be present at a density of greater than 5 pmol/$mm^2$, greater than 6 pmol/$mm^2$, greater than 7 pmol/$mm^2$, greater than 8 pmol/$mm^2$, greater than 9 pmol/$mm^2$, greater than 10 pmol/$mm^2$, greater than 12 pmol/$mm^2$, greater than 15 pmol/$mm^2$, or greater than 20 pmol/$mm^2$ of the surface of the microcarrier. It will be understood that the amount of polypeptide present can vary depending on the composition of the microcarrier base (e.g., the density of pendant carboxylic acid groups), the size of the microcarrier base and the nature of the polypeptide itself. It will be further understood that it may be difficult to determine the surface density of polypeptide, as some detected polypeptide may be grafted internally in the microcarrier. However, it has been determined that good cell attachment can be achieved in serum-free conditions when the overall polypeptide density is in a range of 10 nmol to 500 nmol polypeptide per milligram of dry microcarrier, e.g., between about 50 nmol polypeptide/mg dry microcarrier and about 100 nmol polypeptide/mg dry microcarrier.

A polypeptide may be conjugated to the polymerized microcarrier via any suitable technique. A polypeptide may be conjugated to a polymerized microcarrier via an amino terminal amino acid, a carboxy terminal amino acid, or an internal amino acid. One suitable technique involves 1-ethyl-3-[3-dimethylaminopropyl]carbodiimide hydrochloride (EDC)/N-hydroxysuccinimide (NHS) chemistry, as generally known in the art. EDC and NHS or N-hydroxysulfosuccinimide (sulfo-NHS) can react with carboxyl groups of the microcarrier base to produce amine reactive NHS esters. EDC reacts with a carboxyl group of the microcarrier base to produce an amine-reactive O-acylisourea intermediate that is susceptible to hydrolysis. The addition of NHS or sulfo-NHS stabilizes the amine-reactive O-acylisourea intermediate by converting it to an amine reactive NHS or sulfo-NHS ester, allowing for a two step procedure. Following activation of the microcarrier base, the polypeptide may then be added and the terminal amine of the polypeptide can react with the amine reactive ester to form a stable amide bond, thus conjugating the polypeptide to the microcarrier base. When EDC/NHS chemistry is employed to conjugate a polypeptide to the microcarrier, the N-terminal amino acid is preferably an amine containing amino acid such as lysine, ornithine, diaminobutyric acid, or diaminoproprionic aicd. Of course, any acceptable nucleophile may be employed, such as hydroxylamines, hydrazines, hydroxyls, and the like.

EDC/NHS chemistry results in a zero length crosslinking of polypeptide to microcarrier. Linkers or spacers, such as poly(ethylene glycol) linkers (e.g., available from Quanta BioDesign, Ltd.) with a terminal amine may be added to the N-terminal amino acid of polypeptide. When adding a linker to the N-terminal amino acid, the linker is preferably a N-PG-amido-$PEG_X$-acid where PG is a protecting group such as the Fmoc group, the BOC group, the CBZ group or any other group amenable to peptide synthesis and X is 2, 4, 6, 8, 12, 24 or any other discrete PEG which may be available. In some embodiments, amino acids may serve as linkers to project a cell binding region of a polypeptide away from the surface of the microcarrier In various embodiments, a 1 μM-2500 μM polypeptide fluid composition, such as a solution, suspension, or the like, is contacted with an activated microcarriers to conjugate the polypeptide. For example the polypeptide concentration may be between about 100 μM and about 2000 μM, between about 500 μM and about 1500 μM, or about 1000 μM. It will be understood that the volume of the polypeptide composition and the concentration may be varied to achieve a desired density of polypeptide conjugated to the microcarrier.

The polypeptide may be cyclized or include a cyclic portion. Any suitable method for forming cyclic polypeptide may be employed. For example, an amide linkage may be created by cyclizing the free amino functionality on an appropriate amino-acid side chain and a free carboxyl group of an appropriate amino acid side chain. Also, a di-sulfide linkage may be created between free sulfydryl groups of side chains appropriate amino acids in the peptide sequence. Any suitable technique may be employed to form cyclic polypeptides (or portions thereof). By way of example, methods described in, e.g., WO1989005150 may be employed to form cyclic polypeptides. Head-to-tail cyclic polypeptides, where the polypeptides have an amide bond between the carboxy terminus and the amino terminus may be employed. An alternative to the disulfide bond would be a diselenide bond using two selenocysteines or mixed selenide/sulfide bond, e.g., as described in Koide et al, 1993, Chem. Pharm. Bull. 41(3): 502-6; Koide et al., 1993, Chem. Pharm. Bull. 41(9):1596-1600; or Besse and Moroder, 1997, Journal of Peptide Science, vol. 3, 442-453.

Polypeptides may be synthesized as known in the art (or alternatively produced through molecular biological techniques) or obtained from a commercial vendor, such as American Peptide Company, CEM Corporation, or GenScript Corporation. Linkers may be synthesized as known in the art or obtained from a commercial vendor, such as discrete polyethylene glycol (dPEG) linkers available from Quanta BioDesign, Ltd.

In various embodiments, the polypeptide includes a sequence of Ac-Lys-Gly-Pro-Gln-Val-Thr-Arg-Gly-Asp-Val-Phe-Thr-Met-Pro-NH2 (SEQ ID NO: 1) or Ac-Lys-Gly-Gly-Asn-Gly-Glu-Pro-Arg-Gly-Asp-Thr-Tyr-Arg-Ala-Tyr-NH2 (SEQ ID NO: 2). Of course, it will be understood that any polypeptide may be used, particularly polypeptides containing an Arg-Gly-Asp sequence.

C. Blocking Carboxylic Groups by Derivation

Following grafting of the polypeptide to the microcarrier base, remaining unconjugated carboxylic acid functional groups (or a portion thereof) of the base may be blocked. For example, the carboxylic acid groups may be blocked via derivatization with a monoamine. Such blocking converts highly hydrophilic carboxylic acid groups to less hydrophilic amide group, which decreases the hydrophillicity of the microcarrier and thus alters the water regain and EWC of the microcarrier. As a consequence the blocking alters the stiffness of the hydrogel microcarrier material. That is, decreasing the water content increases the stiffness of the microcarrier. Accordingly, the stiffness and swellability of the microcarrier can be readily tuned, as desired, to impact cell behavior, without having to control crosslinking density. Thus, the stiffness may be modified after the microcarrier base has been manufactured (after the cross-linking density has been fixed).

If EDC/NHS chemistry is used to graft the peptide to the microcarrier base, excess activated ester (resulting from the pendant COOH moeties) of the microcarrier base can be readily deactivated via monoamine blocking to produce a resulting amide. Of course, blocking by derivatization may be performed in any suitable manner.

Any suitable low molecular weight monoamine may be used for blocking the carboxylic acid groups. Examples of suitable monoamines that may be used include ammonia, hydroxylamine, methylamine, ethyl amine, ethanolamine, methoxyethylamine, n-propylamine, isopropylamine, hydroxyl-propylamine, butylamine, tert-butylamine, sec-butylamine, and the like. It will be understood that the monoamine selected will have an effect on the water regain and EWC of the microcarrier, and thus may be preselected based on the desired properties.

Blocking of the carboxylic acid groups by reaction with excess monoamine typically reduces the number of carboxylic acid groups by about 2 fold to about 4 fold. Complete blocking is generally not achieved due to hydrolysis during blocking. Accordingly, the surface of the microcarrier (without accounting for the polypeptide) tends to remain slightly negative (at physiological, cell culture pH). However, blocking conditions may be adjusted to increase or decrease the efficiency of blocking as desired.

Following blocking, the surface of the microcarrier (except for perhaps portions of the conjugated polypeptide) may be free of positive charge at cell culture pH, and would be neutral or negatively charged. While not intending to be bound by theory, it is believed that the negative charge, or at least the lack of positive charge, would repel cells from the surface. This could lead to decreased or minimal non-specific binding of cultured cells to the microcarrier base surface so that bio-specific interaction between the conjugated polypeptide and cell receptors drive the interaction between the cells and the microcarriers. The reduction of non-specific binding allows for the interaction to be controlled, which can result in better reproducibility of results, such a cellular differentiation or the lack thereof.

2. Cell Culture Articles

Microcarriers as described herein may be used in any suitable cell culture system. Typically microcarriers and cell culture media are placed in a suitable cell culture article and the microcarriers are stirred or mixed in the media. Suitable cell culture articles include bioreactors, such as the WAVE BIOREACTOR® (Invitrogen), single and multi-well plates, such as 6, 12, 96, 384, and 1536 well plates, jars, petri dishes, flasks, multi-layered flasks, beakers, plates, roller bottles, tubes, bags, membranes, cups, spinner bottles, perfusion chambers, bioreactors, CellSTACK® culture chambers (Corning Incorporated) and fermenters.

3. Incubating Cells in Culture Media Having Microcarriers Containing Conjugated Polypeptide A cell culture article housing culture media containing conjugated polypeptide as described above may be seeded with cells. The cells may be of any cell type. For example, the cells may be connective tissue cells, epithelial cells, endothelial cells, hepatocytes, skeletal or smooth muscle cells, heart muscle cells, intestinal cells, kidney cells, or cells from other organs, stem cells, islet cells, blood vessel cells, lymphocytes, cancer cells, primary cells, cell lines, or the like. The cells may be mammalian cells, preferably human cells, but may also be non-mammalian cells such as bacterial, yeast, or plant cells.

In numerous embodiments, the cells are stem cells which, as generally understood in the art, refer to cells that have the ability to continuously divide (self-renewal) and that are capable of differentiating into a diverse range of specialized cells. In some embodiments, the stem cells are multipotent, totipotent, or pluripotent stem cells that may be isolated from an organ or tissue of a subject. Such cells are capable of giving rise to a fully differentiated or mature cell types. A stem cell may be a bone marrow-derived stem cell, autologous or otherwise, a neuronal stem cell, or an embryonic stem cell. A stem cell may be nestin positive. A stem cell may be a hematopoeietic stem cell. A stem cell may be a multi-lineage cell derived from epithelial and adipose tissues, umbilical cord blood, liver, brain or other organ. In various embodiments, the stem cells are pluripotent stem cells, such as pluripotent embryonic stem cells isolated from a mammal. Suitable mammals may include rodents such as mice or rats, primates including human and non-human primates. In various embodiments, the microcarrier with conjugated polypeptide supports undifferentiated culture of embryonic stem cells for 5 or more passages, 7 or more passages, or 10 or more passages. Typically stems cells are passaged to a new surface after they reach about 75% confluency. The time for cells to reach 75% confluency is dependent on media, seeding density and other factors as know to those in the art.

Because human embryonic stem cells (hESC) have the ability to grown continually in culture in an undifferentiated state, the hESC for use with microcarriers as described herein may be obtained from an established cell line. Examples of human embryonic stem cell lines that have been established include, but are not limited to, H1, H7, H9, H13 or H14 (available from WiCell established by the University of Wisconsin) (Thompson (1998) *Science* 282:1145); hESBGN-01, hESBGN-02, hESBGN-03 (BresaGen, Inc., Athens, Ga.);

HES-1, HES-2, HES-3, HES-4, HES-5, HES-6 (from ES Cell International, Inc., Singapore); HSF-1, HSF-6 (from University of California at San Francisco); I 3, I 3.2, I 3.3, I 4, I 6, I 6.2, J 3, J 3.2 (derived at the Technion-Israel Institute of Technology, Haifa, Israel); UCSF-1 and UCSF-2 (Genbacev et al., Fertil. Steril. 83(5):1517-29, 2005); lines HUES 1-17 (Cowan et al., NEJM 350(13):1353-56, 2004); and line ACT-14 (Klimanskaya et al., Lancet, 365(9471):1636-41, 2005). Embryonic stem cells may also be obtained directly from primary embryonic tissue. Typically this is done using frozen in vitro fertilized eggs at the blastocyst stage, which would otherwise be discarded.

Other sources of pluripotent stem cells include induced primate pluripotent stem (iPS) cells. iPS cells refer to cells, obtained from a juvenile or adult mammal, such as a human, that are genetically modified, e.g., by transfection with one or more appropriate vectors, such that they are reprogrammed to attain the phenotype of a pluripotent stem cell such as an hESC. Phenotypic traits attained by these reprogrammed cells include morphology resembling stem cells isolated from a blastocyst as well as surface antigen expression, gene expression and telomerase activity resembling blastocyst derived embryonic stem cells. The iPS cells typically have the ability to differentiate into at least one cell type from each of the primary germ layers: ectoderm, endoderm and mesoderm. The iPS cells, like hESC, also form teratomas when injected into immuno-deficient mice, e.g., SCID mice. (Takahashi et al., (2007) Cell 131(5):861; Yu et al., (2007) Science 318: 5858).

To maintain stem cells in an undifferentiated state it may be desirable to minimize non-specific interaction or attachement of the cells with the surface of the microcarrier, while obtaining selective attachment to the polypeptide(s) attached to the surface. The ability of stem cells to attach to the surface of a microcarrier without conjugated polypeptide may be tested prior to conjugating polypeptide to determine whether the microcarrier provides for little to no non-specific interaction or attachement of stem cells. Once a suitable microcarrier has been selected, cells may be seeded in culture medium containing the microcarriers.

Prior to seeding cells, the cells may be harvested and suspended in a suitable medium, such as a growth medium in which the cells are to be cultured once seeded. For example, the cells may be suspended in and cultured in a serum-containing medium, a conditioned medium, or a chemically-defined medium. As used herein, “chemically-defined medium” means cell culture media that contains no components of unknown composition. Chemically defined cell culture media may, in various embodiments, contain no proteins, hydrosylates, or peptides of unknown composition. In some embodiments, chemically defined media contains polypeptides or proteins of known composition, such as recombinant growth hormones. Because all components of chemically-defined media have a known chemical structure, variability in culture conditions and thus variability in cell response can be reduced, increasing reproducibility. In addition, the possibility of contamination is reduced. Further, the ability to scale up is made easier due, at least in part, to the factors discussed above. Chemically defined cell culture media are commercially available from Invitrogen (Invitrogen Corporation, 1600 Faraday Avenue, PO Box 6482, Carlsbad, Calif. 92008) as STEM PRO, a fully serum- and feeder-free (SFM) specially formulated from the growth and expansion of embryonic stem cells, Xvivo (Lonza), and Stem Cell Technologies, Inc. as mTeSR1™ maintenance media for human embryonic stem cells.

One or more growth or other factors may be added to the medium in which cells are incubated with the microcarriers conjugated to polypeptide. The factors may facilitate cellular proliferation, adhesion, self-renewal, differentiation, or the like. Examples of factors that may be added to or included in the medium include muscle morphogenic factor (MMP), vascular endothelium growth factor (VEGF), interleukins, nerve growth factor (NGF), erythropoietin, platelet derived growth factor (PDGF), epidermal growth factor (EGF), activin A (ACT) such as activin A, hematopoietic growth factors, retinoic acid (RA), interferons, fibroblastic growth factors, such as basic fibroblast growth factor (bFGF), bone morphogenetic protein (BMP), peptide growth factors, heparin binding growth factor (HBGF), hepatocyte growth factor, tumor necrosis factors, insulin-like growth factors (IGF) I and II, transforming growth factors, such as transforming growth factor-β1 (TGFβ1), and colony stimulating factors.

The cells may be seeded at any suitable concentration. Typically, the cells are seeded at about 10,000 cells/$cm^2$ of microcarrier to about 500,000 cells/$cm^2$. For example, cells may be seeded at about 50,000 cells/$cm^2$ of substrate to about 150,000 cells/$cm^2$. However, higher and lower concentrations may readily be used. The incubation time and conditions, such as temperature, $CO_2$ and $O_2$ levels, growth medium, and the like, will depend on the nature of the cells being cultured and can be readily modified. The amount of time that the cells are cultured with the microcarriers may vary depending on the cell response desired.

The cultured cells may be used for any suitable purpose, including (i) obtaining sufficient amounts of undifferentiated stem cells cultured on a synthetic surface in a chemically defined medium for use in investigational studies or for developing therapeutic uses, (ii) for investigational studies of the cells in culture, (iii) for developing therapeutic uses, (iv) for therapeutic purposes, (v) for studying gene expression, e.g. by creating cDNA libraries, (vi) for studying drug and toxicity screening, and (vii) the like.

One suitable way to determine whether cells are undifferentiated is to determine the presence of the OCT4 marker. In various embodiments, the undifferentiated stems cells cultured on microcarriers as described herein for 5, 7, or 10 or more passages retain the ability to be differentiated.

In an aspect, a microcarrier for cell culture, comprising: a cross-linked polysaccharide hydrogel microcarrier base having a neutral or negative charge at pH 7; and a polypeptide conjugated to the base. In an aspect, a microcarrier according to aspect 1 is provided, wherein the microcarrier consists essentially of the neutral or negatively charged cross-linked polysaccharide hydrogel microcarrier base and the cell attachment polypeptide conjugated to the base. In an aspect, (3) microcarrier according to aspects 1 or 2 is provided, wherein the neutral or negatively charged cross-linked polysaccharide hydrogel microcarrier base comprises carboxylic acid functional groups. In an aspect (4) a microcarrier according to aspect 3 is provided, wherein the microcarrier base comprises the reaction product of a monoamine with a carboxylic acid functional group. In an aspect (5), a microcarrier according to any of aspects 1-4 is provided, wherein the microcarrier base comprises dextran. In an aspect (6), a microcarrier according any of aspects 1-5 is provided, wherein the cell attachment polypeptide comprises an amino acid sequence of RGD. In an aspect (7), a microcarrier according to any of aspects 1-5 is provided, wherein the synthetic cell attachment polypeptide is selected from the group consisting of a BSP polypeptide, a vitronectin polypeptide, and a fibronectin polypeptide. In an aspect (8), a microcarrier according to any of aspects 1-7 is provided, wherein the microcarrier has a water regain of between 30 ml/g and 50 ml/g. In an aspect (9) microcarrier according to any of aspects 1-8 is provided wherein the microcarrier base is produced by reaction of a polysaccharide hydrogel having pendant carboxylic acid groups with a monoamine, wherein the polysaccharide hydro gel having pendant carboxylic acid groups has between 1.5 milliequivalents carboxylic acid groups per gram of the base and 5 milliequivalents carboxylic acid groups per gram of the base prior to conjugation with the polypeptide.

In an aspect (10), a method for forming a cell culture microcarrier is provided, comprising: providing a net negatively or neutral charged polysaccharide hydrogel microcarrier base having pendant carboxylic acid functional groups; and conjugating a synthetic polypeptide to a carboxylic acid group of the microcarrier base to form the microcarrer. In an aspect (11) a method according to aspect 10, wherein the microcarrier base has between 1.5 milliequivalents carboxylic acid groups per gram of the base and 5 milliequivalents carboxylic acid groups per gram of the base prior to conjugation with the polypeptide is provided. In an aspect (12) a method according to aspect 10 is provided, further comprising blocking at least some of the carboxylic acid functional groups with a monoamine to form an amide. In an aspect (13) a method according to aspect 12 is provided, wherein the monoamine is selected from the group consisting of ammonia, hydroxylamine, methylamine, ethylamine, ethanolamine, methoxyethaline, n-propylamine, isopropylamine, hydroxyl-propylamine, butylamine, tert-butylamine, and sec-butylamine. In an aspect (14) a method according to aspect 12 is provided, wherein all, or essentially all, of the carboxylic acid groups are blocked. In an aspect (15) a method according to aspect 12, wherein blocking the carboxylic acid functional groups with the monoamine produces a microcarrier having an equilibrium water content of between 10% and 70% is provided. In an aspect (16) a method according to any of aspects 10-15 is provided, wherein the microcarrier base comprises dextran. In an aspect (17) a method according any of aspects 10-16 is provided, wherein the synthetic polypeptide comprises an amino acid sequence of RGD. In an aspect (18) a method according to any of aspects 10-16 is provided, wherein the synthetic polypeptide is selected from the group consisting of a BSP polypeptide, a vitronectin polypeptide, and a fibronectin polypeptide. In an aspect (19) a method for culturing cells, comprising: contacting cells with a cell culture medium having microcarriers, wherein the microcarrier comprises (i) a neutral or negatively charged polysaccharide hydrogel microcarrier base, and (ii) a polypeptide conjugated to the base, wherein the polypeptide comprises and RGD amino acid sequence; and culturing the cells in the medium is provided. In an aspect (20) the method of aspect 19 is provided, wherein the cells are stem cells and the medium is a chemically defined medium.

In the following, non-limiting examples are presented, which describe various embodiments of the microcarriers and methods discussed above.

EXAMPLES

Example 1

Vitronectin (VN) Conjugation to Dextran Beads 100 milligrams dry carboxymethylated dextran beads, CM-Sephadex® C-50 beads ([CAS Number 9047-08-], available from GE Healthcare), were weighed in an plastic tube and suspended in 10 milliliters of 200 mM EDC and 50 mM NHS aqueous solution. The suspension was left for 30 minutes to swell the beads and to activate the carboxylic acid groups. Then the activated microcarriers were collected by centrifugation and rinsed three times with 10 ml of deionized water. After rinsing, they were resuspended in 15 ml borate buffer pH 9.2 containing 61.2 mg of vitronectin peptide (Ac-Lys-Gly-Pro-Gln-Val-Thr-Arg-Gly-Asp-Val-Phe-Thr-Met-Pro-NH2, SEQ ID NO: 1), available from American Peptide Company, Inc., catalog number: 341587) and left to react for 2 hours.

A general overview of the reaction scheme is shown in FIG. 1, which shows a schematic carboxylated bead reacted with EDC/NHS in water and VN-peptode/borate at pH 9.2 (1) followed by ethanolamine blocking (2) to arrive at a peptide-conjugated, blocked bead.

The peptide conjugated microcarriers were collected by centrifugation and washed three times with 10 ml PBS buffer pH 7.4. Finally, the excess activated ester was deactivated by blocking with 10 ml 1M ethanolamine pH 8.4 for 60 minutes. The peptide grafted and blocked microcarriers (noted CMD-VN) were collected and rinsed three times with PBS. After removal of the excess of PBS, the microcarriers were rinsed 2 times with 70:30% v/v ethanol/water and stored in this ethanol/water solution before cell culture.

Example 2

Rhodamine-Labeled Peptide Conjugation to Dextran Beads

Figure 2:
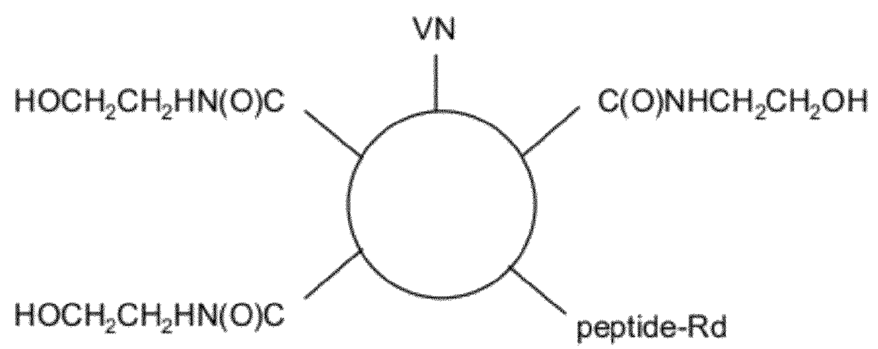
FIG. 2 is a picture showing idealized structure of both vitronectin-peptide and rhodamine-labeled peptide conjugated to carboxymethyl dextran beads utilized for the quantification of conjugated peptide.

The same procedure as described in EXAMPLE 1 was reproduced except that rhodamine-labeled fluorescent peptide (ref 347678 from American Peptide Company Inc. CA USA, having amino acid sequence 5/6TAMRA-Gly-Arg-Gly-Asp-Ser-Pro-Ile-Ile-Lys-NH2, SEQ ID NO. 3) was admixed with vitronectin peptide from EXAMPLE 1. Briefly, activation of the microcarrier was performed as described in EXAMPLE 1 except that 153 microliter of 1 mM rhodamine-labeled peptide was added to 15 ml borate buffer containing 61.2 mg of vitronectin peptide for the conjugation step. The blocking step was done as in EXAMPLE 1. A schematic diagram of a resulting bead in shown in FIG. 2.

Conjugation of VN and rhodamine-labeled peptide worked well and no non-specific adsorption of the peptides occurred when activation was omitted (data not shown.

Figure 3:
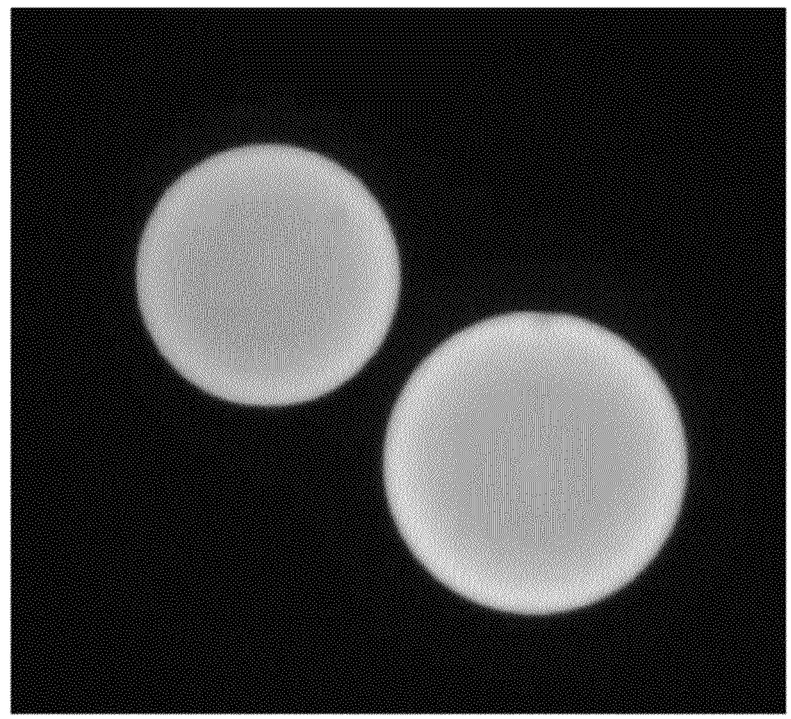
FIG. 3 is a fluorescent picture of beads showing the good uniformity of the grafted peptides.

FIG. 3 is a micrographic image showing a fluorescently labeled bead with good uniformity of the grafted peptides observed.

The rhodamine-labled peptide was used to show that conjugation can be achieved (see FIG. 3) as expected, but also used to establish the relationship existing between concentration of the peptide used for the conjugation and amount of peptide grafted to the beads. The results of which are shown in FIG. 4.

Figure 4:
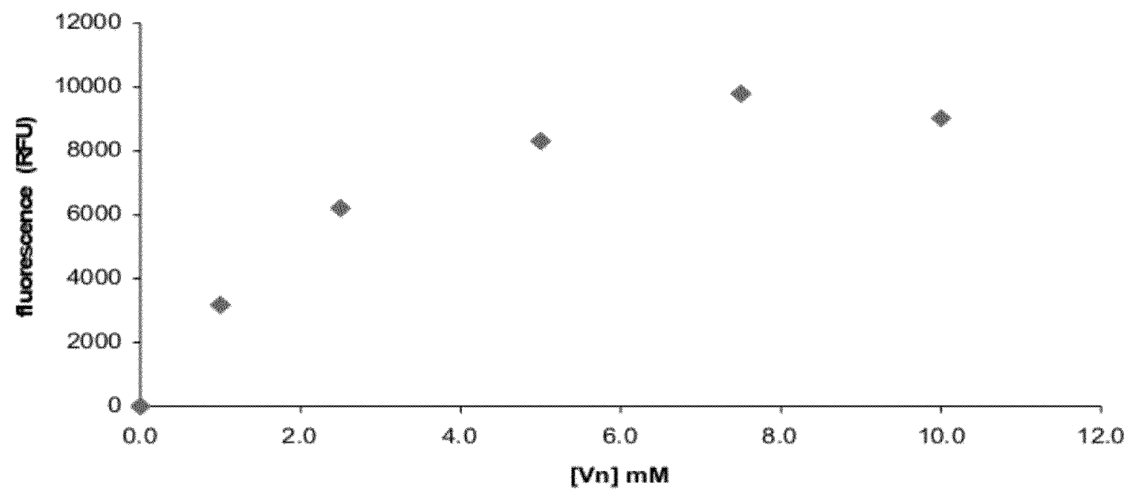
FIG. 4 is a graph showing fluorescence data from vitronectin peptide/Rhodamine-labeled peptide conjugated beads as a function of the vitronectin peptide concentration used for conjugation step.

To produce the results presented in FIG. 4, after blocking, rinsing with PBS and removal of the excess of PBS by centrifugation, the fluorescent peptide conjugated beads were not resuspended in the ethanol/water mixture as described in EXAMPLE 1. Instead, 100 microliters of swollen beads were introduced in three wells of a 96 well plate (triplicate). Fluorescence was measured using a Synergy™ 4 plate reader from BioTek. Set up used is given below.

| | |
|---|---|
| Plate Type | 96 WELL PLATE |
| Read | Fluorescence Endpoint |
| | A1 . . . H12 |

-continued

| Filter Set 1 |
| --- |
| Excitation: 530/25, Emission: 590/20 |
| Mirror: Top 550 nm, Sensitivity: 35 |
| Light Source: Tungsten, Standard |
| Dynamic Range |
| Read Speed: Normal, Delay: 100 msec. |
| Measurement/Date Point: 10 |
| Top Probe Offset: 7 mm |

Example 3

RGE Peptide Conjugation to Dextran Beads (Negative Control)

Figure 8:
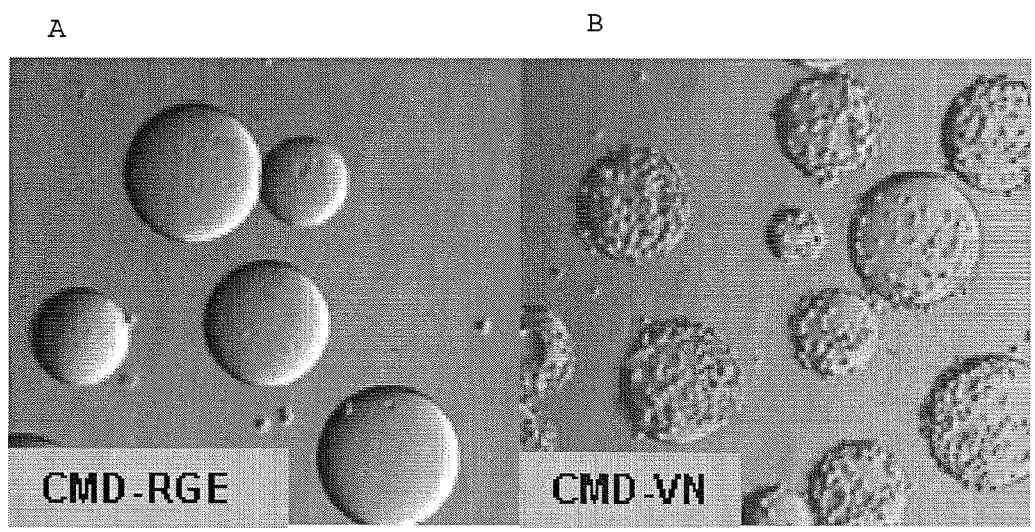
FIG. 8 is a phase contrast microscopy image of HT1080 cells after incubation with carboxymethyl dextran beads grafted with either RGE polypeptides FIG. 8(A) or vitronectin polypeptides FIG. 8(B). Cell adhesion is only observed on vitronectin peptide grafted beads.

The same procedure as described in EXAMPLE 1 was reproduced except that RGE-peptide (ref 348454 (ID#RGE) from American peptide Company Inc. CA USA, having amino acid sequence Ac-Gly-Arg-Gly-Glu-Ser-Pro-Ile-Ile-Lys-NH2, SEQ ID NO:4) was utilized instead of the vitronectin peptide from EXAMPLE 1. These microcarriers grafted with a peptide containing an RGE core are noted CMD-RGE and were used as a negative control. The obtained RGE-functionalized microcarrier does not support cell attachment, as expected for a negative control, and indicated that adhesion on VN peptide-conjugated microcarrier is mainly due to peptide-specific adhesion (see FIG. 8). Cell culture conditions are described in more detail below in EXAMPLE 5.

Example 4

Grafted Peptide Quantification

Bicinchoninic acid (BCA) mixture reagent from a BCA assay kit (Interchim S.A., Montlucon, France) was prepared by adding 800 microliters of reagent B to 40 ml of reagent A and mixing.

Microcarriers were prepared as described in EXAMPLE 1 except that after blocking, rinsing with PBS and removal of the excess of PBS by centrifugation, the beads were not resuspended in the ethanol/water mixture. Instead, 500 microliters of swollen beads were introduced in a glass vial. Then, 4 ml of BCA mixture reagent are added and left for 2 hours with slight shaking every 30 min.

The microcarrier was removed by centrifugation and the supernatant is collected. 225 microliters of the supernatant was added to three wells of a 96 well plate (triplicate) and the absorbance at 562 nm was measured using the plate reader.

The "Blank" correspond to the absorbance measured on unmodified CM-Sephadex® C-50 beads.

Figure 5:
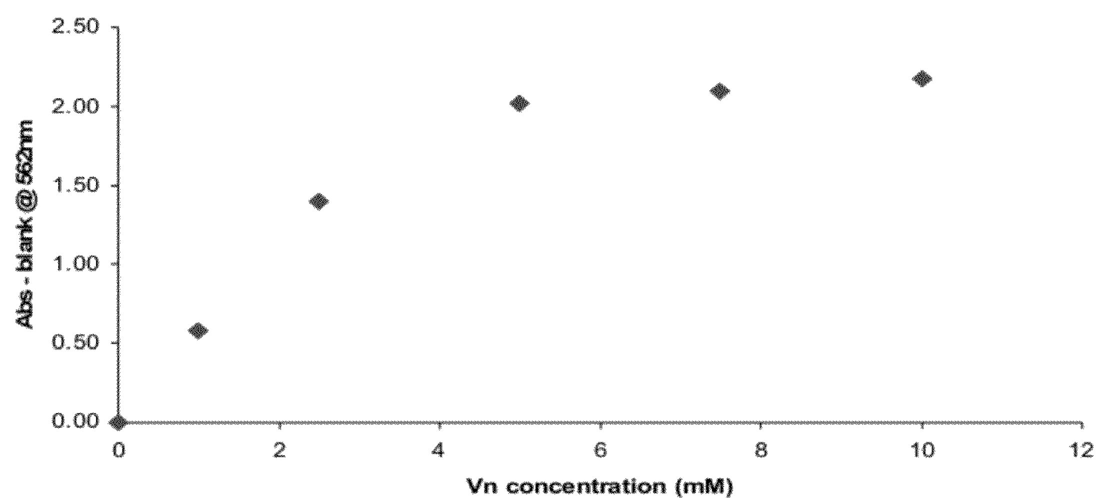
FIG. 5 is a graph showing the BCA assay results for the vitronectin peptide/Rhodamine-labeled peptide conjugated beads as a function of the vitronectin peptide concentration used for conjugation step.

FIG. 5 shows absorbance as a function of the concentration of vitronectin-peptide used for conjugation step.

As shown in both FIGS. 4 and 5, polypeptide grafting to the microcarriers was achieved.

Example 5

Cell Adhesion Assays Using HT1080 Cells

For adhesion assays, 5 mg of VN peptide-grafted microcarriers were washed in D-PBS, saturated with bovine serum albumin (BSA), resuspended in serum free culture medium and transferred to 24 wells multiwell ultralow attachment (ULA) plates.

HT1080 human fibrosarcoma cells (ATCC #CCL-121) were grown in Iscove's Modified Dulbecco's Medium (IMDM) (Gibco) supplemented with 10% foetal bovine serum (FBS) and penicillin streptomycin antibiotics. Cells were kept in an incubator at 37° C., in a humid atmosphere with 5% CO2. Cells were split as needed by trypsinization before they reached confluency.

Figure 6:
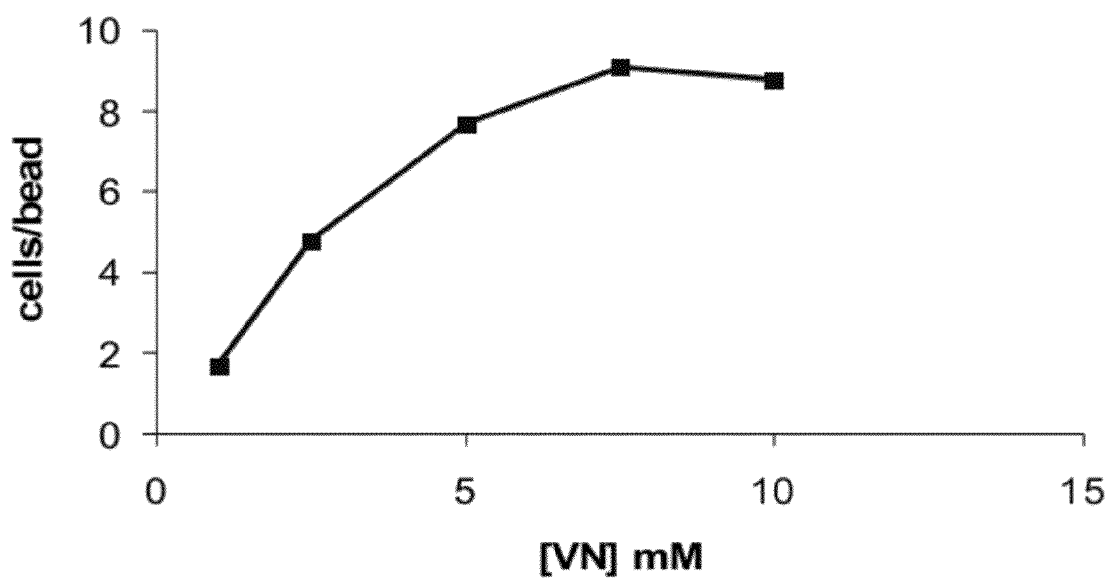
FIG. 6 is a graph representing the number of visible HT1080 cells adhering to vitronectin peptide grafted carboxymethyl dextran beads 2 hours after seeding, in function of the vitronectin peptide concentration used for conjugation.

HT1080, cells were trypsinized washed and counted, and 300,000 cells in serum free medium were mixed with the beads previously prepared. Plates were incubated 2 hours at 37° C. and cell adhesion was observed using phase contrast microscopy. When quantification was needed, the preparation was fixed using 3.7% formaldehyde in PBS and images of the cells adhering on the carriers were acquired. The number of imaged carriers and of visible cells adhering on the carriers was determined, and the number of cell per bead was calculated. Results are presented in FIG. 6, which shows that the number of cells/bead increased as the VN-peptide concentration increased. It is worth noting that a fairly good relationship exits between amount of peptide grafted to the microcarrier, determined by fluorescence and BCA assay (see FIG. 4 and FIG. 5, respectively), and the amount of cell attached to the microcarrier.

Figure 7:
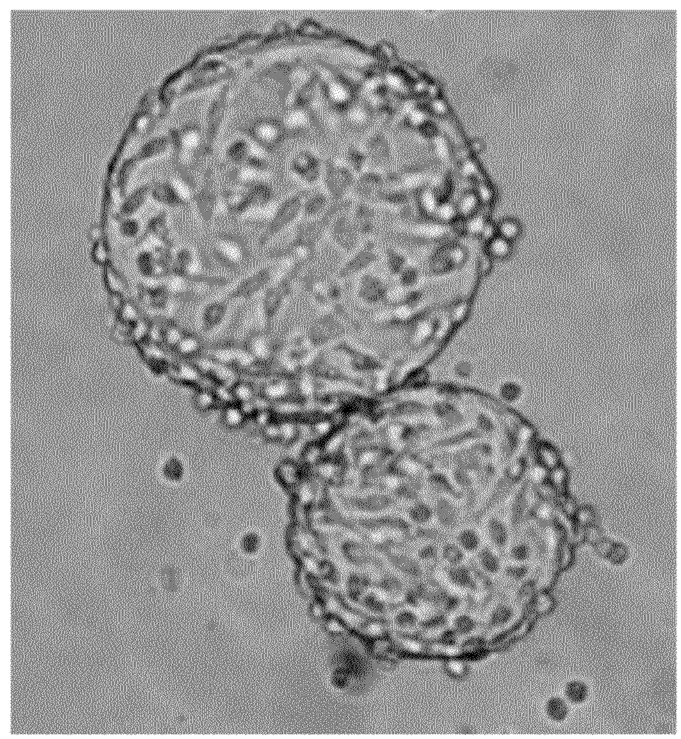
FIG. 7 is a phase contrast microscopy image of HT1080 cells adhered to vitronectin peptide grafted carboxymethyl dextran beads 2 hours after seeding.

A representative image of HT1080 cells adhered to VN-CMD microcarriers is depicted in FIG. 7, which is a phase contrast microscopy image taken two hours after seeding. As briefly discussed above with regard to EXAMPLE 3, no adhesion of HT1080 cells was observed on CMD microcarriers with grafted RGE polypeptide (CMD-RGE), but was observed on CMD-VN microcarriers, suggesting that the cell binding is peptide-specific and that little to no non-specific binding to the microcarrier base occurs (see FIG. 8).

Figure 9:
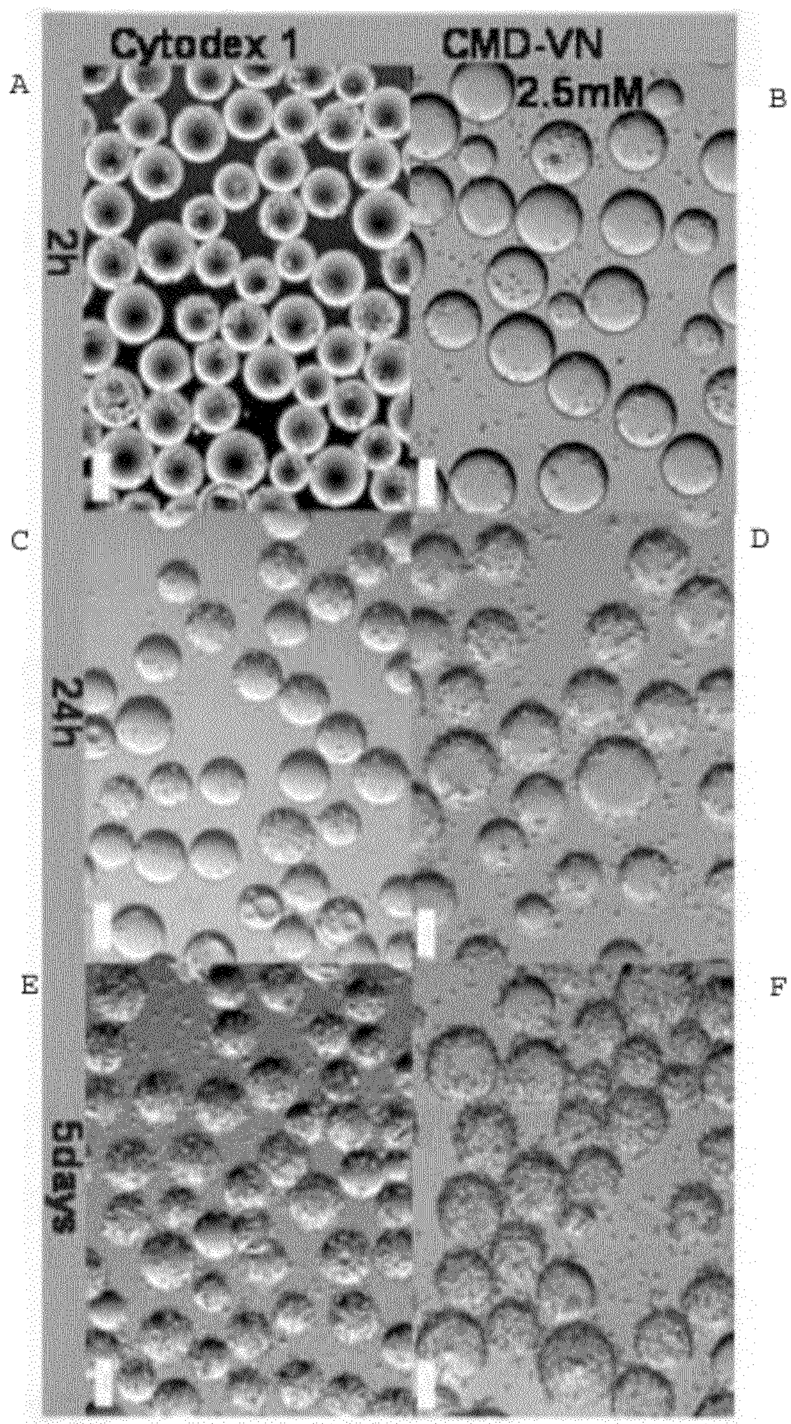
FIG. 9A-F is a series of phase contrast microscopy pictures illustrating HT1080 cell adhesion and growth in stirred culture, on Cytodex™ 1 (GE HEALTHCARE BIO-SCIENCES AB LTD) microcarriers and on vitronectin grafted carboxymethyl dextran beads. The pictures represent the cells 2 hours, 24 hours and 5 days after seeding on the beads.

The ability of the anchorage-dependent HT1080 cells to bind and expand on CMD-VN microcarriers was compared to Cytodex™ 1 microcarriers (GE Healthcare Biosciences AB Ltd), which are positively charged and are believe to support non-specific binding of anchorage-dependent cells. The culture conditions for the Cytodex™ 1 beads were as described above with regard to CMD-VN microcarriers, except that Cytodex™ 1 beads were substituted for CMD-VN microcarriers, and the experiment was performed in spinner flask under stirred conditions. As shown in FIG. 9, HT1080 cells adhered to and expanded on CMD-VN microcarriers as well as, or better than, on Cytodex 1 beads. The phase contrast images in FIG. 9 were taken 2 hours, 24 hours, and 5 days after seeding the cells on the microcarriers.

Figure 10:
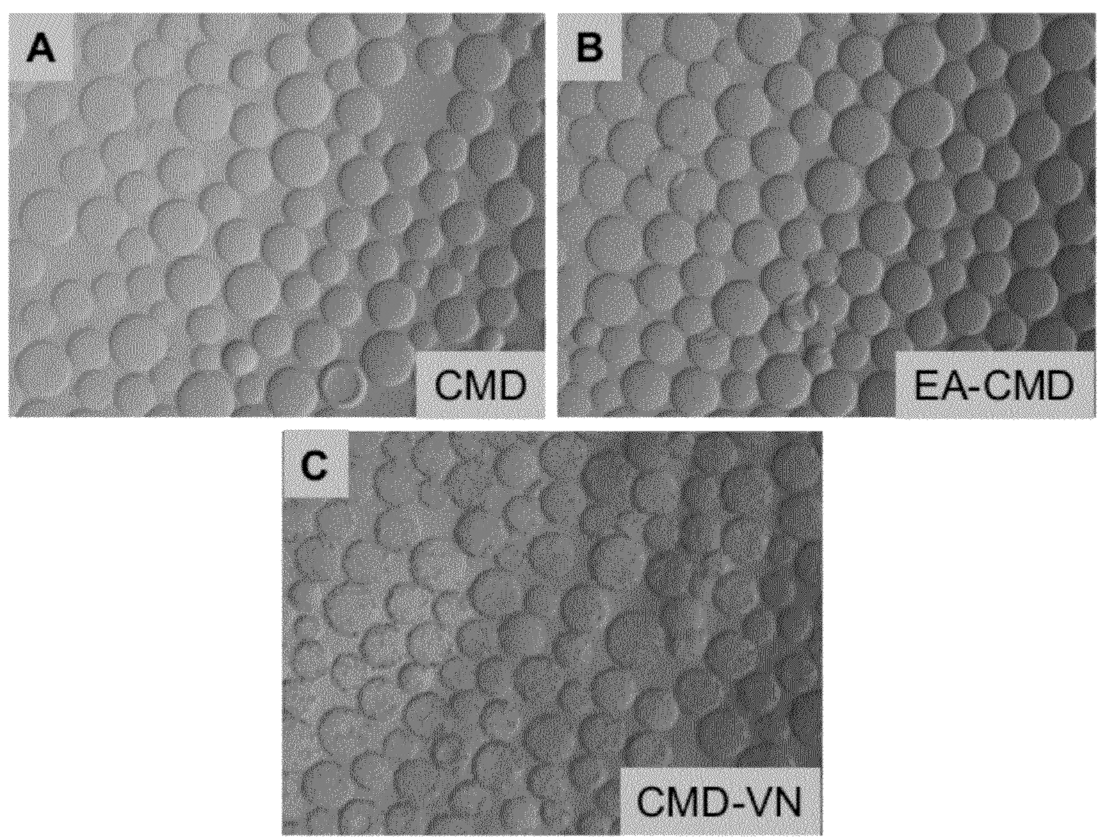
FIGS. 10A-C are phase contrast microscopy images of different carboxymethyl dextran (CMD) microcarrier beads after incubation with HT1080 cells. A: untreated CMD microcarriers without grafted vitronectin polypeptide; B: ethanolamine blocked CMD (EA-CMD) microcarriers without grafted vitronectin polypeptide; C: ethanolamine blocked CMD beads with grafted vitronectin polypeptide (CMD-VN).

To support the contention that attachment of the anchorage dependent HT1080 cells was peptide- or biospecific, the ability of cells to adhere to untreated carboxymethyl dextran (CMD) beads or ethalonamine blocked CMD breads without conjugated VN-peptide was compared to blocked CMD beads with grafted VN-peptide. The beads were prepared as described above. Briefly, 5 mg of beads were incubated for 1 hours in PBS 1% BSA, washed 2 times in PBS and resuspended in serum free IMDM. HT1080 cells were collected from a culture plate by trypsination, cells were washed, counted and $5\times10^5$ cells were mixed with the beads prepared in a well from a 24 well plate. Cells were incubated for 1 hour at 37° C., and then fixed by adjusting the medium to 3.7% formaldehyde. Beads were washed to remove non bound cells and representative photographs were taken. The results obtained are presented in FIG. 10. As shown in FIG. 10, cell adhesion is only observed when the VN peptide is conjugated to the CMD beads (panel C, CMD-VN), untreated beads (panel A, CMD) or ethanolamine blocked beads (panel B, EA-CMD) without grafted VN-peptide do not support cell adhesion in the conditions tested. Thus, the binding appears to be peptide-specific. These results also support the contention that anchorage dependent cells do not bind well, if at all, to neutral to negatively charged hydrogel microcarriers.

Figure 11:
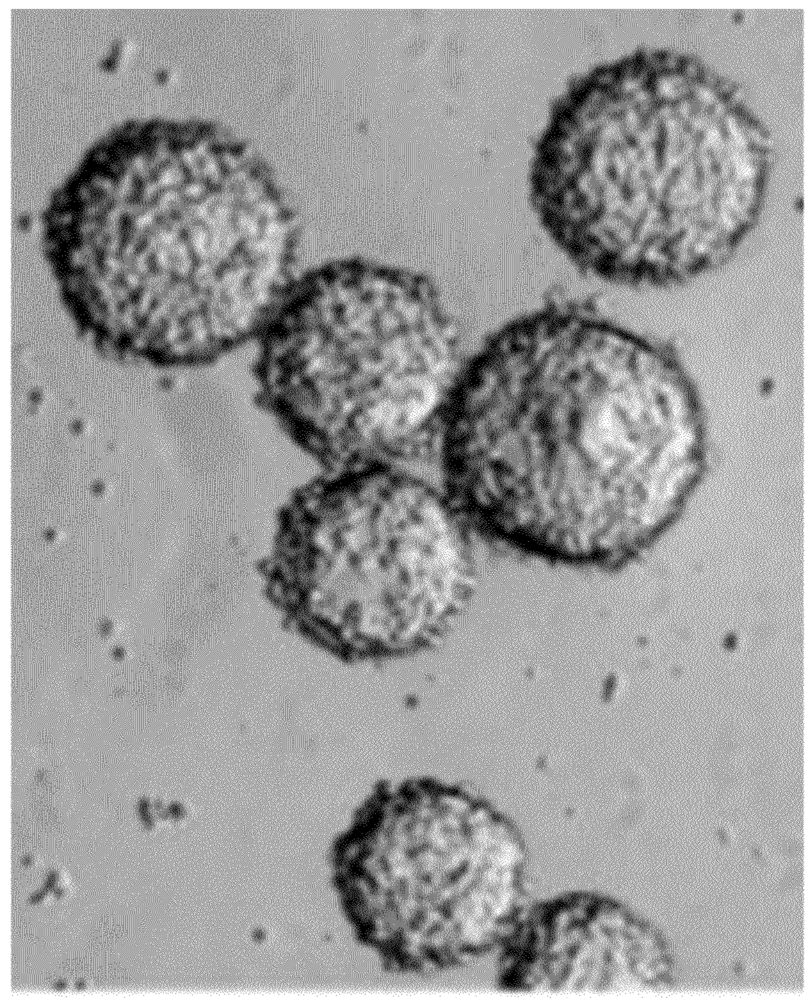
FIG. 11 is a phase contrast microscopy image of HT1080 cells reaching confluency after 5 days of growth in stirred culture on vitronectin peptide grafted carboxymethyl dextran beads.

The ability of HT1080 cells to remain bound and grow on CMD-VN microcarriers under stirred culture conditions was also examined. Briefly, 100 mg of peptide-grafted microcarriers, or commercially available microcarriers (cytodex 1, cytodex 3, SoloHill Pronectin® F) were washed in D-PBS, resuspended in culture medium and transferred to a 125 mL spinner flask (Corning, Inc.). HT1080 cells were trypsinized and counted, and 2,500,000 cells were mixed with the beads previously prepared. After an initial 2 hour adhesion period in a final medium volume of 10 mL without agitation, the medium volume was adjusted to 30 mL and the agitation was setup to 15 minutes every hour. Samples were collected daily and evaluated by phase contrast microscopy. A phase contrast image showing HT 1080 cells reaching confluency after 5 days in the stirred culture with CMD-VN microcarriers is presented in FIG. 11.

Figure 12:
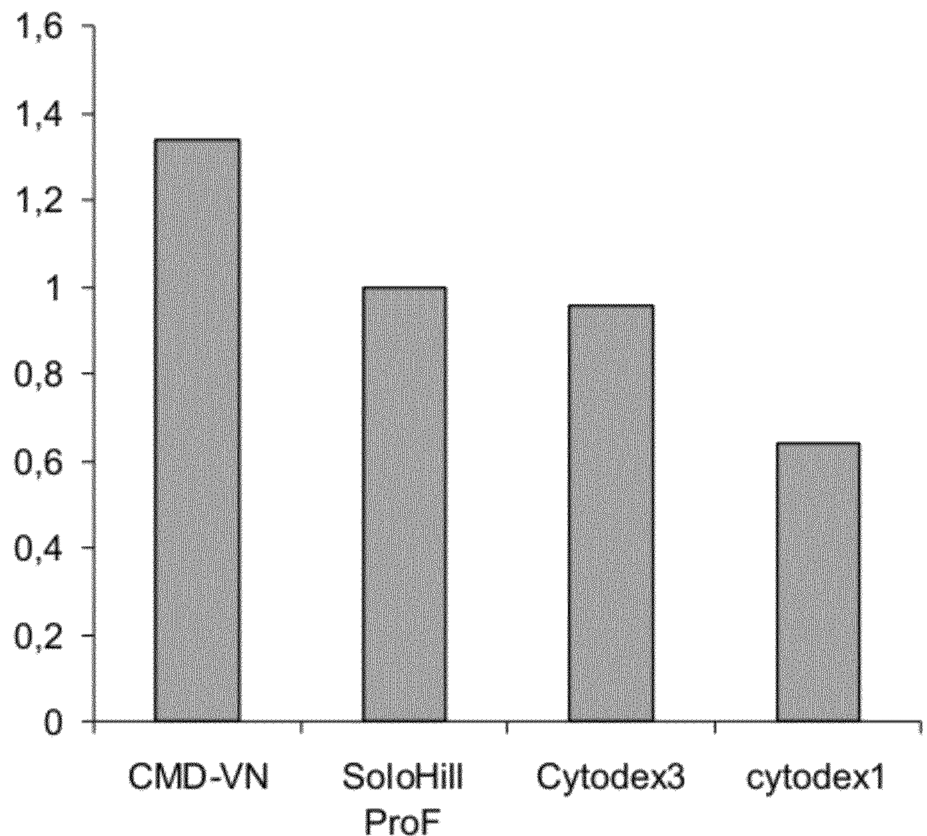
FIG. 12 is a histogram comparing HT1080 cell growth after 5 days in a stirred culture on different types of microcarriers. Final cell number was reported to the growth measured on SoloHill Pronectin®F microcarriers.

The ability of HT1080 cells to grow on a variety of different micocarriers was also examined under stirred conditions. In addition to Cytodex 1 beads and CMD-VN microcarriers, HT1080 cells were cultured on Cytodex 3 (GE Healthcare Biosciences AB Ltd) and Pronectin®F microcarriers (SoloHill Engineering, Inc). Cytodex 3 beads are a collagen-coated bead and Pronectin F (ProF) microcarriers include a positively charged polystyrene microcarrier base with grafted recombinant fibronectin. For cell expansion 100 mg of peptide-grafted microcarriers, or commercially available microcarriers (cytodex 1, cytodex 3, SoloHill Pronectin® F) were washed in D-PBS, resuspended in culture medium and transferred to a 125 mL spinner flask (Corning, Inc.). Cell seeding and culture were perfomed as described above. After 4 to 5 days, cell-bearing carriers were collected by centrifugation, washed in PBS buffer, and the cells were harvested by trysinization. The number of living cells was determined by counting with a Malassez cell after trypan blue exclusion test. The results are presented in FIG. 12, where the final cell number is reported to the growth measured on ProF microcarriers. As shown in FIG. 12, the anchorage dependent HT1080 cells grew better on the CMD-VN microcarriers than on the Cytodex 1™, Cytodex 3™, and ProF microcarriers.

The results presented herein show that polysaccharide-based hydrogel microcarriers having neutral to negatively charged surfaces with conjugated adhesion polypeptide, such as CMD-VN microcarriers, can support attachment and growth of anchorage-dependent cells, such as HT1080 cells, in a peptide-specific manner in serum free conditions. The binding of the cells to such microcarriers is sufficient to support culture under stirred conditions. Further, despite the net neutral to negative charge and the lack of non-specific binding, the cells appear to attach and grow better on such microcarriers than on other commercially available microcarriers.

Example 6

Cell Adhesion Assays Using Nulli-SCC1 Cells

For adhesion assays, 5 mg of RGE peptide-conjugated microcarrier (negative control), VN peptide-grafted microcarriers or SoloHill ProNectin F microcarrier were washed in D-PBS, saturated with BSA, resuspended in serum free culture medium and transferred to 24 wells multiwell ULA plates.

NULLI-SCC1 murine teratocarcinoma cells (ATCC #CRL-1566) were grown in IMDM medium (Gibco) supplemented with 10% FBS and penicillin streptomycin antibiotics. Cells were grown on gelatin coated plates, kept at 37° C., in a humid atmosphere with 5% CO2. The growth medium was replaced every other day, and cells were split as needed by trypsinization before they reach confluency.

NULLI SCC1, cells were trypsinized and counted, and 500,000 cells were mixed with the beads previously prepared and incubated in MTeSR serum free medium. Initial adhesion was observed after 2 hours. The plates were then incubated for 16 more hours at 37° C., and cell adhesion was observed again after this time using phase contrast microscopy (see FIG. 13).

Figure 13:
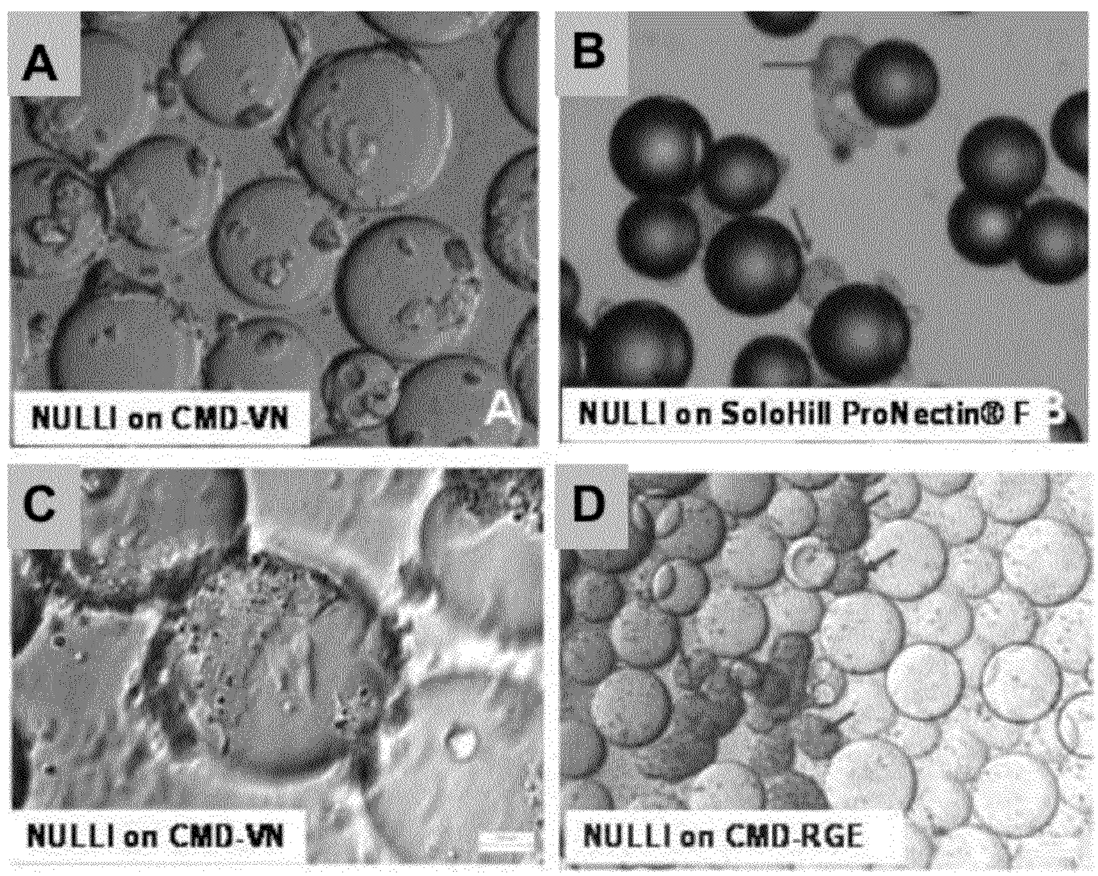
FIG. 13A-D is a series of phase contrast microscopy pictures illustrating NULLI SCC-1 cell adhesion on peptide grafted carboxymethyl dextran microcarriers. Panel A illustrates the homogeneity of cell colonies repartition 24 hours after seeding on vitronectin peptide grafted carboxymethyl dextran beads. Panel B illustrates the morphology of the cells incubated in the same condition than on SoloHill Pronectin®F microcarriers, with the preferential formation of non adherent embryonic bodies like structures indicated by the arrows. Panel C is a close up illustrating the formation of cell colonies on vitronectin peptides grafted microcarriers. Panel D illustrates the lack of adhesion on RGE peptides grafted beads and the formation of non adherent embryonic bodies like structures.

As shown in panel A of FIG. 13, the homogeneity of cell colonies repartition 24 hours after seeding on vitronectin peptide grafted carboxymethyl dextran beads. As shown in panel B of FIG. 13, the morphology of the cells incubated in the same conditions, but on SoloHill Pronectin®F microcarriers, preferentially form non-adherent embryonic bodies like structures indicated by the arrows. Panel C of FIG. 13 shows a close up image illustrating the formation of cell colonies on vitronectin peptides grafted microcarriers. Panel D of FIG. 13 illustrates the lack of adhesion on RGE peptides grafted beads and the formation of non adherent embryonic bodies like structures.

As expected, the RGE peptide-conjugated microcarriers do not support cell adhesion, and only suspended embryoid bodies like aggregates were observed. Despite their rich RGD peptide coating, the SoloHill ProNectin F microcarriers showed poor cell attachment and only anchored embryoid bodies like structures were observed. On the contrary, spread colonies were obtained with the microcarriers prepared in accordance with EXAMPLE 1.

Example 7

48 Hour Adhesion of Pluripotent Mouse Embryonic Stem Cells

For long term adhesion assays, 5 mg of VN peptide-grafted microcarriers or Cytodex 3 microcarriers were washed in D-PBS, resuspended in serum free culture medium (mTeSR, StemCell Technologies) and transferred to 24 wells multiwell ULA plates.

ES-D3 pluripotent mouse stem embryonic stem cells (ATCC #CRL-11632) were grown in DMEM medium supplemented with 15% FBS and 0.1 mM beta-mecaptoethanol as recommended by ATCC. Cells were routinely grown on Matrigel coated plates, and trypsinized and diluted before they reach confluency.

Figure 14:
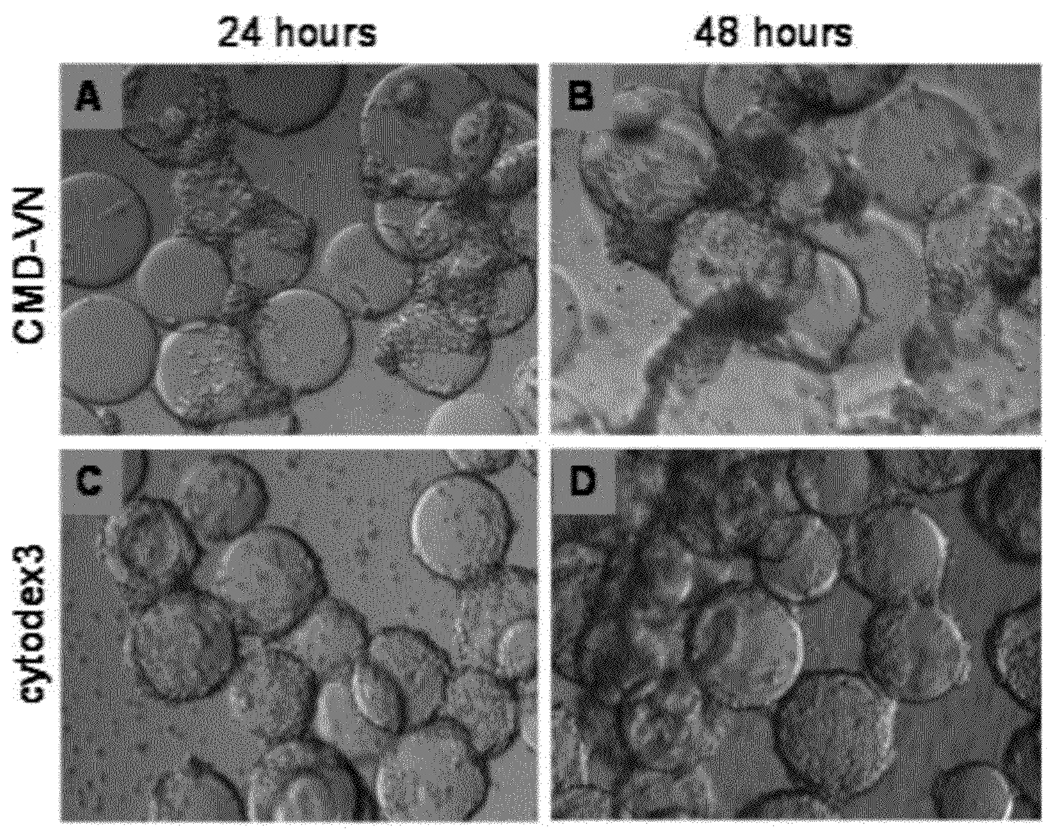
FIG. 14A-E is a series of phase contrast microscopy pictures illustrating ES-D3 mouse pluripotent embryonic stem cells on peptide grafted carboxymethyl dextran microcarriers in serum free conditions and in the presence of 10 μM of Y27632 ROCK kinase inhibitor. A and B illustrate cell adhesion at 24 and 48 hours on CMD-VN beads in mTeSR1 medium supplemented with 10 μM Y27632. C and D illustrate ES-D3 cell adhesion on Cytodex3 microcarriers after 24 and 48 hours respectively in mTeSR medium supplemented with 10 μM Y27632. E corresponds to the alkaline phosphatase activity in cell extracts performed at the end of the experiment. A negative control was performed with STO mouse fibroblasts.

ES-D3 cells were trypsinized, washed and counted. $1\times10^6$ cells were resuspended in mTeSR serum free medium, mixed with the beads previously prepared and 10 μM of Y27632 ROCK inhibitor (sigma ref #Y-0503) were added to each well to inhibit cell/cell contacts and prevent excessive microcarriers aggregation. Plates were incubated for 48 hours at 37° C., and cell adhesion was observed at 24 and 48 hours using phase contrast microscopy (see FIG. 14). Pluripotent mouse embryonic stem cells are able to adhere nicely to the microcarriers tested. We observe that, despite the lack of agitation, the tendency of the microcarriers to form aggregates is limited.

Cell pluripotency was investigated at the end of the experiment by dosing the activity of alkaline phosphatase, an enzyme specifically expressed by pluripotent embryonic stem cells. The results obtained indicate that the cells pluripotency is maintained as expected in a way comparable to what is observed on the positive control (Cytodex3). STO mouse fibroblasts (ATCC #CRL-1503) grown on TCT as recommended by ATCC are used as a negative control, as expected cells are not pluripotent and do not express alkaline phosphatase.

However, the results support the suggestion that the microcarriers described herein will support culture of pluripotent stem cells, such as human embryonic stem cells.

Example 8

Adhesion and Expansion of Human Embryonic Stem Cells

BG01V/hOG cells (Invitrogen) were maintained on Matrigel coated TCT 75 Flask (Corning) in serum free mTERS1 medium containing 50 ug/ml Hygromycin B (STEMCELL Technologie). Daily medium changes began after the first 48 h in culture. Cells were passaged every 5 to 6 days using collagenase IV (Invitrogen) and mechanical scraping.

For the assay, aggregate colonies were harvested and resuspended in fresh mTeSR1 serum free medium. Cells were seeded to the 24 wells Corning Ultra low attachment microplate (1.5×105 cells per cm2) containing the VN-peptide grafted CMD microcarriers, prepared as described above, or Cytodex™ 3 microcarrier available from GE Healthcare as a comparative example. The volume was adjusted to 600 microliters with culture medium. Cells were allowed to attach to the microcarriers for 48 h without agitation. Two days after seeding, cellular attachment and spreading was assessed using Ziess Axiovert 200M inverted microscope. Quantitative analysis was also performed as followed. The media was removed and the beads were washed in the wells with D-PBS (2×3 mL). The D-PBS was removed and replaced with 200 microliters of CellTiter-Glo reagent (Promega). Microplate was place in the shaker for 10 min at room temperature and luminescence was measured. For the cell expansion assay, same seeding protocol was used and cells were maintained in static condition over the course of cell expansion. After 48 h cell attachment, culture medium was changed daily after sedimentation of the cells and the beads. After 5 days, cell spreading and cell quantification was assessed using the same methods describe above.

Figure 15:
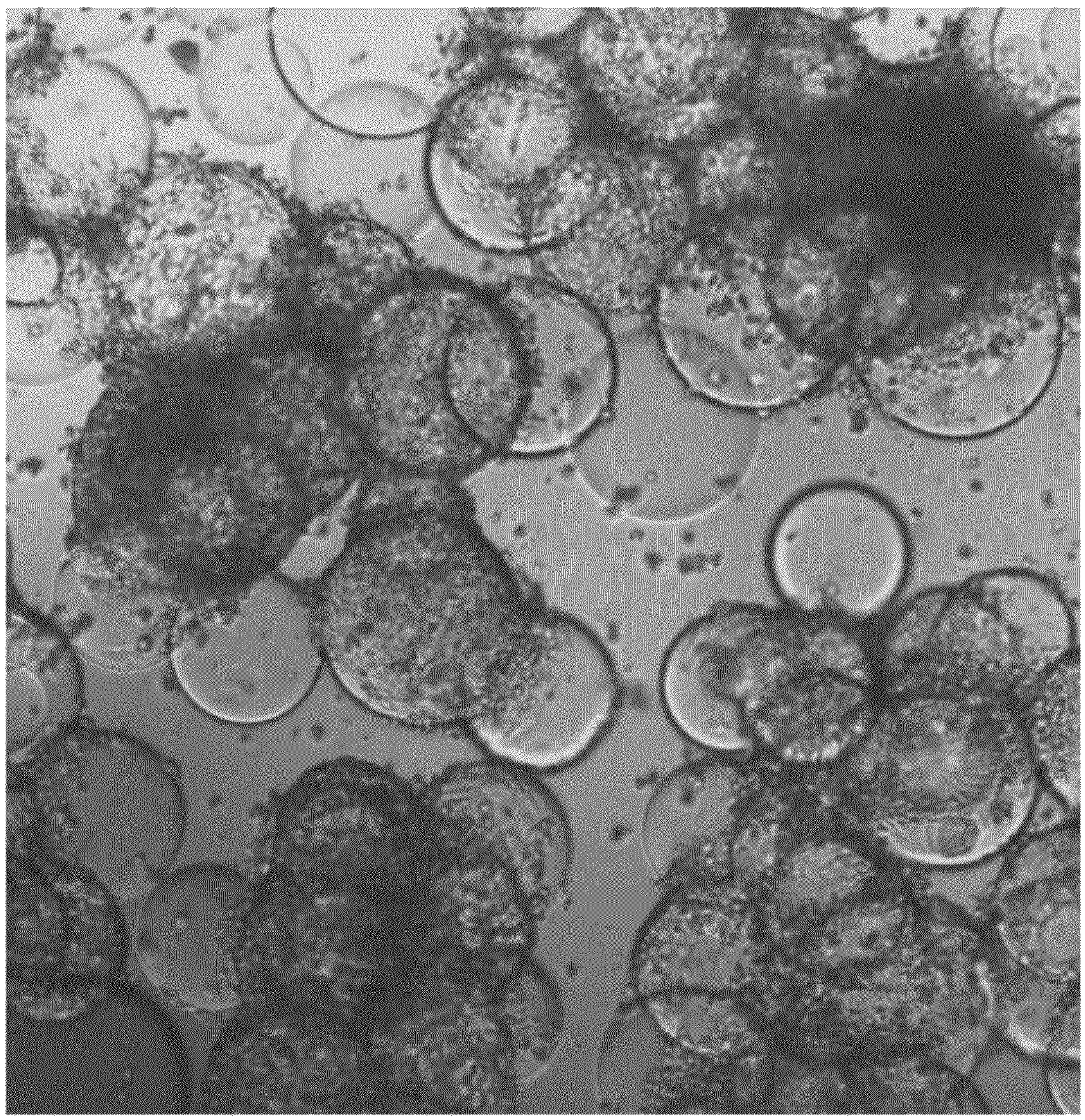
FIG. 15 is a microscopy image illustrating BG01V cells attachment on peptide grafted carboxymethyl dextran microcarriers 5 days after seeding.
Figure 16:
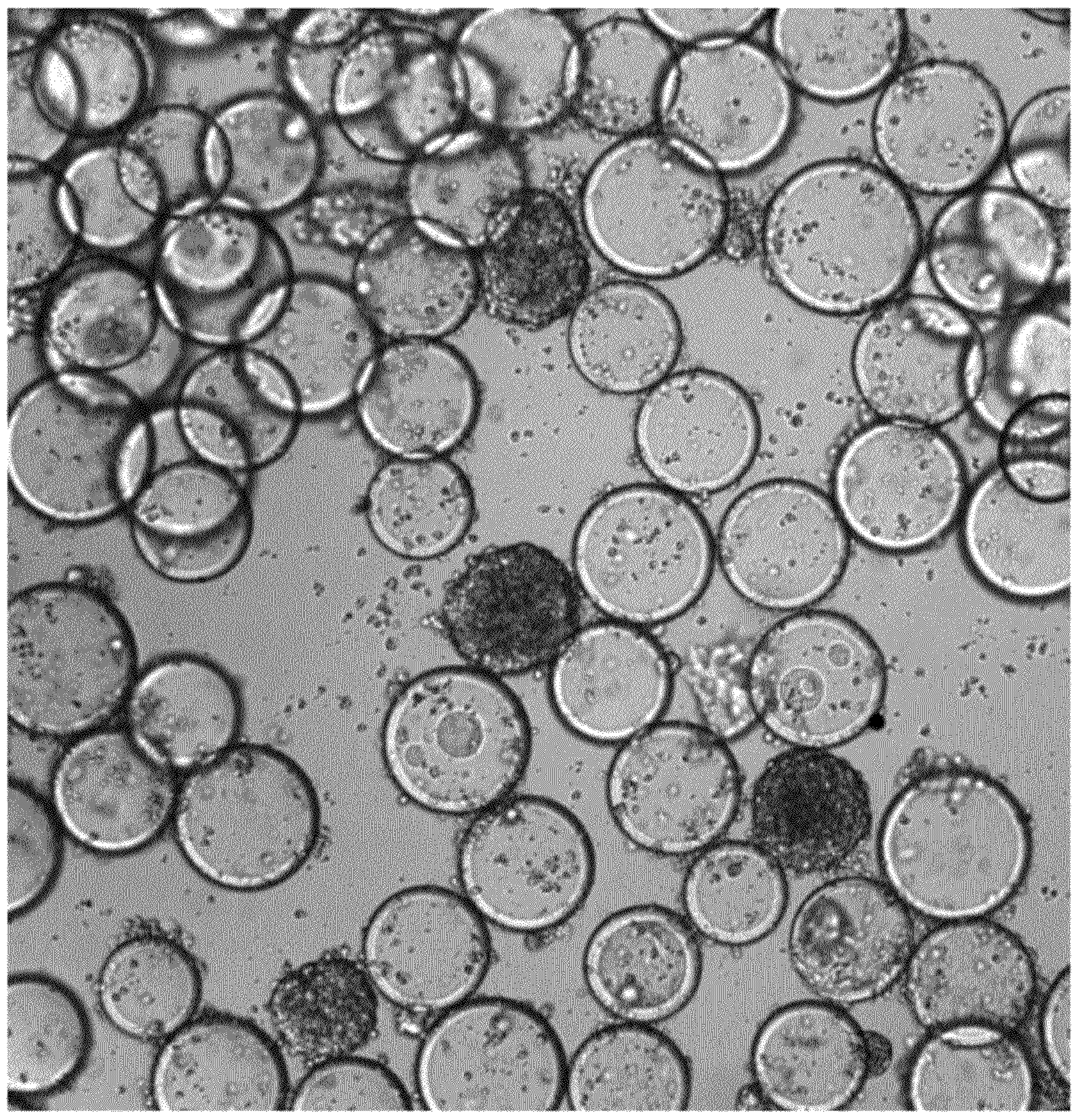
FIG. 16 is a microscopy image illustrating floating embryonic bodies formation when BG01V cells are incubated with Cytodex 3 microcarriers (as a comparative example).
Figure 17:
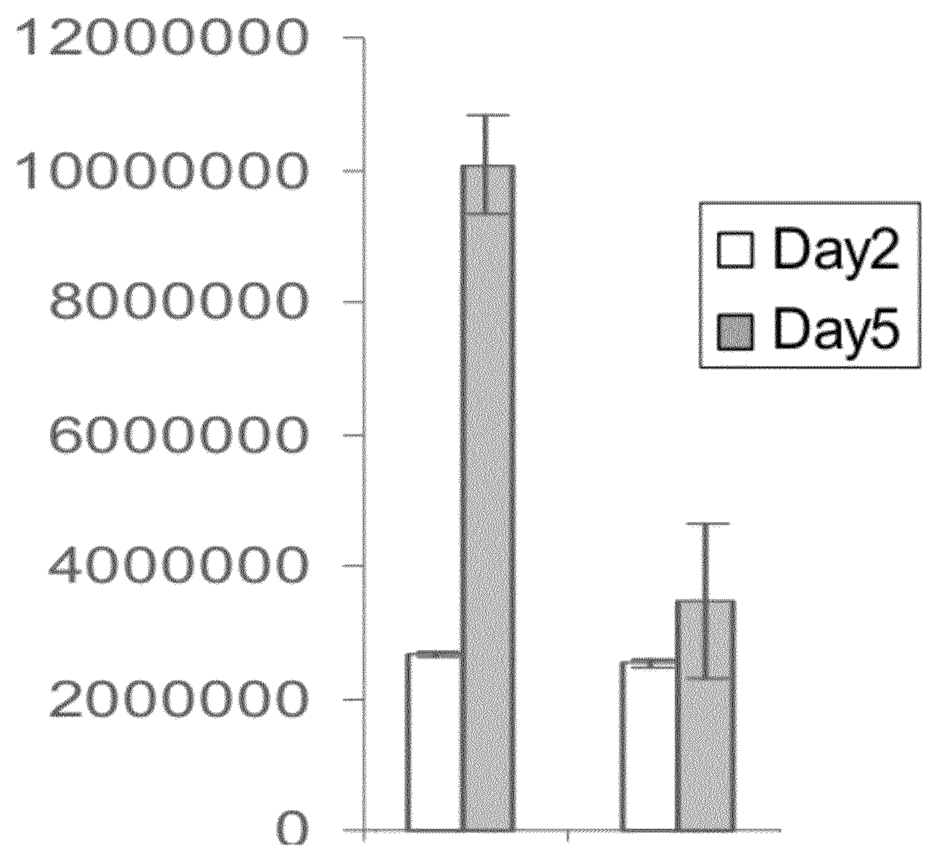
FIG. 17 is a Graph showing the quantification of BG01V cell after 2 days and 5 days culture performed on peptide grafted carboxymethyl dextran microcarriers (CMD-VN) and Cytodex™ 3 as comparative example.

As shown in FIG. 15, one can observe a nice spreading of BG01V/hOG cell colonies on CMD-VN beads. On Cytodex 3 beads the cells were not able to adhere and instead formed floating embryonic bodies as shown in FIG. 16. As shown in FIG. 17, which is a graph of the quantification of BG01V cells after two days and 5 days culture performed on CMD-VN and Cytodex 3 microcarriers, the cells were maintained and grew significantly better on the CMD-VN microcarriers than on the Cytodex 3 beads, particularly after 5 days of culture.

Thus, embodiments of Synthetic Polysaccharide Microcarriers for Culturing Cells are disclosed. One skilled in the art will appreciate that the microcarriers and methods described herein can be practiced with embodiments other than those disclosed. The disclosed embodiments are presented for purposes of illustration and not limitation.

What is claimed is:

1. A microcarrier for cell culture, comprising:

a cross-linked polysaccharide hydrogel microcarrier base having a net neutral or negative charge in medium at pH 6-8, wherein the cross-linked polysaccharide hydrogel microcarrier base comprises carboxylic acid functional groups, and wherein the cross-linked polysaccharide hydrogel microcarrier base is free of positively charged functional groups in the medium at pH 6-8; and a plurality of synthetic, cell attachment polypeptides conjugated to the base, wherein each of the plurality of synthetic, cell attachment polypeptides is conjugated to the base via one of the carboxylic acid functional groups, wherein each of the plurality of synthetic, cell attachment polypeptides comprises an amino acid sequence of RGD, and wherein at least some of the carboxylic acid functional groups are unconjugated to the plurality of synthetic, cell attachment polypeptides and are blocked with a monoamine, such that the cross-linked polysaccharide hydrogel microcarrier base does not support non-specific attachment of cells thereto during cell culture.

2. A microcarrier according to claim 1, wherein the microcarrier consists essentially of the net neutral or negatively charged cross-linked polysaccharide hydrogel microcarrier base and the plurality of synthetic, cell attachment polypeptides conjugated to the base.

3. A microcarrier according to claim 1, wherein the microcarrier has an equilibrium water content of between 10% and 70%.

4. A microcarrier according to claim 1, wherein the microcarrier base comprises dextran.

5. A microcarrier according to claim 1, wherein each of the plurality of synthetic, cell attachment polypeptides is independently selected from the group consisting of a BSP polypeptide, a vitronectin polypeptide, and a fibronectin polypeptide.

6. A microcarrier according to claim 1, wherein the microcarrier has a water regain of between 30 ml/g and 50 ml/g.

7. A microcarrier according to claim 1, wherein the carboxylic acid functional groups are pendant carboxylic acid functional groups, and wherein the cross-linked polysaccharide hydrogel base has between 1.5 milliequivalents carboxylic acid functional groups per gram of the base and 5 milliequivalents carboxylic acid functional groups per gram of the base prior to conjugation with the plurality of synthetic cell attachment polypeptides.

8. A microcarrier according to claim 1, wherein each of the plurality of synthetic, cell attachment polypeptides independently comprises SEQ ID NO: 1 or SEQ ID NO: 2.

9. The microcarrier according to claim 1, wherein the cross-linked polysaccharide hydrogel microcarrier base and the plurality of synthetic, cell attachment polypeptides conjugated thereto are effective to achieve bioselective attachment of cells to the plurality of synthetic, cell attachment polypeptides during the cell culture.

10. A method for forming a cell culture microcarrier, comprising:

providing a net negatively or neutral charged polysaccharide hydrogel microcarrier base having pendant carboxylic acid functional groups, wherein the polysaccharide hydrogel microcarrier base is free of positively charged functional groups; and conjugating a plurality of synthetic polypeptides to the microcarrier base, wherein each of the plurality of synthetic polypeptides is conjugated to one of the pendant carboxylic acid functional groups of the microcarrier base to form the microcarrer, wherein each of the plurality of synthetic polypeptides comprises an amino acid sequence of RGD, and blocking at least some of the carboxylic acid functional groups which are unconjugated to the plurality of synthetic polypeptides with a monoamine to form an amide, wherein the blocking alters an equilibrium water content of the microcarrier, such that the polysaccharide hydrogel microcarrier base does not support non-specific attachment of cells thereto during cell culture.

11. A method according to claim 10, wherein the microcarrier base has between 1.5 milliequivalents carboxylic acid functional groups per gram of the base and 5 milliequivalents carboxylic acid functional groups per gram of the base prior to conjugation with the plurality of synthetic polypeptides.

12. A method according to claim 10, wherein the monoamine is selected from the group consisting of ammonia, hydroxylamine, methylamine, ethylamine, ethanolamine, methoxyethaline, n-propylamine, isopropylamine, hydroxylpropylamine, butylamine, tert-butylamine, and sec-butylamine.

13. A method according to claim 10, wherein:

all, or essentially all, of the carboxylic acid groups which are unconjugated to the plurality of synthetic polypeptides are blocked;

the microcarrier base comprises a cross-linked polysaccharide; and an equilibrium water content of the microcarrier is altered without altering a cross-linking density of the cross-linked polysaccharide.

14. A method according to claim 10, wherein blocking the carboxylic acid functional groups which are unconjugated to the synthetic polypeptide with the monoamine produces a microcarrier having an equilibrium water content of between 10% and 70%.

15. A method according to claim 10, wherein the microcarrier base comprises dextran.

16. A method according to claim 10, wherein each of the synthetic polypeptides is independently selected from the group consisting of a BSP polypeptide, a vitronectin polypeptide, and a fibronectin polypeptide.

17. A method for culturing stem cells, comprising:

contacting the stem cells with a cell culture medium having microcarriers, wherein the medium is a chemically defined medium, and wherein the microcarrier comprises:

(i) a net neutral or negatively charged polysaccharide hydrogel microcarrier base, wherein the net neutral or negatively charged polysaccharide hydrogel microcarrier base comprises carboxylic acid functional groups, and wherein the net neutral or negatively charged polysaccharide hydrogel microcarrier base is free of positively charged functional groups, and (ii) a plurality of polypeptides conjugated to the base, wherein each of the plurality of polypeptides is conjugated to the base via one of the carboxylic acid functional groups, wherein each of the plurality of polypeptides comprises an RGD amino acid sequence, and wherein at least some of the carboxylic acid functional groups are unconjugated to the plurality of synthetic, cell attachment polypeptides and are blocked with a monoamine; and culturing the stem cells in the chemically defined medium, wherein non-specific attachment of the stem cells to the microcarrier base is not supported.

18. The method according to claim 17, wherein:

the chemically defined medium is serum free; and the plurality of polypeptides are conjugated to the polysaccharide hydrogel microcarrier base at an overall density of from 10 nmol polypeptide per mg of dry microcarrier to 500 nmol polypeptide per mg of dry microcarrier.

19. The method according to claim 17, wherein the stems cells are cultured in an undifferentiated state for five or more passages.

20. The method according to claim 17, wherein the microcarrier has an equilibrium water content of between 5% and 70%, such that the stem cells may be cultured in an undifferentiated state for at least five passages.

* * * * *